(12) United States Patent
Peng

(10) Patent No.: US 12,048,071 B2
(45) Date of Patent: Jul. 23, 2024

(54) ATOMIZER CORES AND METHODS OF MANUFACTURING THE SAME

(71) Applicant: QV TECHNOLOGIES CORP, Toronto (CA)

(72) Inventor: Xiaofeng Peng, Oakville (CA)

(73) Assignee: QV TECHNOLOGIES CORP, Toronto (CA)

( * ) Notice: Subject to any disclaimer, the term of this patent is extended or adjusted under 35 U.S.C. 154(b) by 0 days.

(21) Appl. No.: 18/276,466

(22) PCT Filed: Feb. 9, 2022

(86) PCT No.: PCT/CA2022/050183
§ 371 (c)(1),
(2) Date: Aug. 9, 2023

(87) PCT Pub. No.: WO2022/170425
PCT Pub. Date: Aug. 18, 2022

(65) Prior Publication Data
US 2024/0040668 A1 Feb. 1, 2024

Related U.S. Application Data

(60) Provisional application No. 63/148,023, filed on Feb. 10, 2021.

(51) Int. Cl.
*H05B 3/06* (2006.01)
*A24F 40/46* (2020.01)
(Continued)

(52) U.S. Cl.
CPC ............. *H05B 3/06* (2013.01); *A24F 40/46* (2020.01); *A24F 40/48* (2020.01); *A61M 11/042* (2014.02);
(Continued)

(58) Field of Classification Search
CPC ... H05B 3/06; H05B 3/12; H05B 3/46; H05B 3/03; H05B 3/40; H05B 6/26;
(Continued)

(56) References Cited

U.S. PATENT DOCUMENTS

| | | |
|---|---|---|
| 4,588,540 A | 5/1986 | Kiefer et al. |
| 4,647,477 A | 3/1987 | DeLuca |

(Continued)

FOREIGN PATENT DOCUMENTS

| | | | | |
|---|---|---|---|---|
| CA | 3106427 A1 | * | 2/2020 | ............. A24B 15/14 |
| CN | 201519640 | | 7/2010 | |

(Continued)

OTHER PUBLICATIONS

International Search Report in PCT/CA2022/050183 dated May 10, 2022.
IPRP in PCT/CA2022/050183 dated Apr. 12, 2023.

*Primary Examiner* — Shawntina T Fuqua
(74) *Attorney, Agent, or Firm* — Manelli Selter PLLC; Edward Stemberger

(57) ABSTRACT

Atomizer cores, atomizer core substrates and methods of manufacturing atomizer core substrates are provided as well as aerosol generating devices incorporating same. In one example, the atomizer core comprises a core body having a first surface and a second surface. The core body includes a substrate and a heater with a plurality of channels extending between the first surface and the second surface for transferring an aerosol precursor from the first surface through the substrate and the heater to the second surface, the heater being adapted to heat the aerosol precursor to form an aerosol at the second surface. In other embodiments an insulator is disposed between the substrate and heater and adapted to insulate the substrate at least partially from heat generated by the heater.

25 Claims, 13 Drawing Sheets

(51) Int. Cl.
  *A24F 40/48* (2020.01)
  *A61M 11/04* (2006.01)
  *H05B 3/12* (2006.01)
  *H05B 3/46* (2006.01)
  *H05B 6/26* (2006.01)

(52) U.S. Cl.
  CPC ........... *H05B 3/12* (2013.01); *A61M 2207/00* (2013.01); *H05B 3/46* (2013.01); *H05B 6/26* (2013.01); *H05B 2203/021* (2013.01)

(58) Field of Classification Search
  CPC .... H05B 2203/021; A24F 40/46; A24F 40/48; A24F 40/10; A24F 40/70; A24F 40/42; A24F 40/44; A24F 40/05; A24F 40/30; A24F 40/40; A24F 40/50; A24F 40/51; A24F 40/53; A24F 40/57; A24F 47/00; A61M 11/042; A61M 2207/00; A61M 15/06; A61M 2205/0211; B05B 7/0012; B05B 7/11686; B05B 17/0676; B05B 17/0607; B05B 17/06; F24H 15/10; F24H 15/219
  See application file for complete search history.

(56) References Cited

U.S. PATENT DOCUMENTS

| | | | |
|---|---|---|---|
| 6,126,723 A | 10/2000 | Drost et al. |
| 7,920,777 B2 | 4/2011 | Rabin et al. |
| 8,881,737 B2 | 11/2014 | Collett et al. |
| 9,861,132 B2 | 1/2018 | Li et al. |
| 9,986,760 B2 | 6/2018 | Macko et al. |
| 10,136,672 B2 | 11/2018 | Minskoff et al. |
| 10,194,694 B2 | 2/2019 | Davis et al. |
| 10,201,185 B2 | 2/2019 | Bleloch et al. |
| 10,272,170 B2 | 4/2019 | Debrief |
| 10,292,429 B2 | 5/2019 | Duc et al. |
| 10,463,077 B2 | 11/2019 | Lau et al. |
| 10,548,351 B2 | 2/2020 | Brammer et al. |
| 11,078,108 B2 | 8/2021 | Peuchert et al. |
| 11,117,068 B2 | 9/2021 | Meinhart et al. |
| 11,272,739 B2 | 3/2022 | Schmidt et al. |
| 11,458,265 B2 | 10/2022 | Brammer et al. |
| 2015/0114409 A1 | 4/2015 | Brammer et al. |
| 2015/0359262 A1 | 12/2015 | Liu et al. |
| 2016/0007653 A1 | 1/2016 | Tu |
| 2016/0138795 A1 | 5/2016 | Meinhart et al. |
| 2017/0105455 A1 | 4/2017 | Qiu |
| 2017/0360100 A1 | 12/2017 | Duc |
| 2017/0367411 A1 | 12/2017 | Duc |
| 2018/0162769 A1 | 6/2018 | Peuchert et al. |
| 2018/0360112 A1 | 12/2018 | Qiu |
| 2019/0006866 A1 | 1/2019 | Zhu |
| 2019/0053539 A1 | 2/2019 | Davis et al. |
| 2019/0098935 A1 | 4/2019 | Phan et al. |
| 2019/0216132 A1 | 7/2019 | Phan et al. |
| 2019/0246696 A1 | 8/2019 | Schmidt et al. |
| 2019/0249929 A1 | 8/2019 | Rush et al. |
| 2020/0163383 A1 | 5/2020 | Kessler et al. |
| 2020/0359704 A1 | 11/2020 | Deng |
| 2021/0052008 A1 | 2/2021 | Han et al. |
| 2021/0161207 A1 | 6/2021 | Li et al. |
| 2021/0227885 A1 | 7/2021 | Sudlow et al. |
| 2022/0117302 A1 | 4/2022 | Kleine et al. |
| 2022/0125114 A1 | 4/2022 | Peng et al. |
| 2022/0338543 A1 | 10/2022 | Shi et al. |
| 2022/0401669 A1 | 12/2022 | Brammer et al. |

FOREIGN PATENT DOCUMENTS

| | | | | |
|---|---|---|---|---|
| CN | 102256386 | | 11/2011 | |
| CN | 106252602 | | 12/2016 | |
| CN | 205831081 | | 12/2016 | |
| CN | 107874322 | | 4/2018 | |
| CN | 108158040 | | 6/2018 | |
| CN | 108887753 | | 11/2018 | |
| CN | 109043668 | | 12/2018 | |
| CN | 109090713 | | 12/2018 | |
| CN | 109123804 | | 1/2019 | |
| CN | 109192521 | | 1/2019 | |
| CN | 109222251 | | 1/2019 | |
| CN | 109363247 | | 2/2019 | |
| CN | 109363248 | | 2/2019 | |
| CN | 109414078 A | * | 3/2019 | ............ A24F 40/10 |
| CN | 109527657 | | 3/2019 | |
| CN | 109619687 | | 4/2019 | |
| CN | 208740113 | | 4/2019 | |
| CN | 109770439 | | 5/2019 | |
| CN | 109820252 | | 5/2019 | |
| CN | 109875125 | | 6/2019 | |
| CN | 110025057 | | 7/2019 | |
| CN | 110051043 | | 7/2019 | |
| CN | 110063529 | | 7/2019 | |
| CN | 110089778 | | 8/2019 | |
| CN | 111109665 | | 5/2020 | |
| CN | 210809287 | | 6/2020 | |
| CN | 210809287 U | | 6/2020 | |
| KR | 20230076057 A | * | 5/2023 | |
| RU | 1794614 | | 2/1993 | |
| RU | 2155729 | | 9/2000 | |
| RU | 2433100 | | 11/2011 | |
| RU | 2018108876 | | 9/2019 | |
| WO | 2020165177 A1 | | 8/2020 | |
| WO | 2021027338 A1 | | 2/2021 | |
| WO | WO-2023035851 A1 | * | 3/2023 | |

* cited by examiner

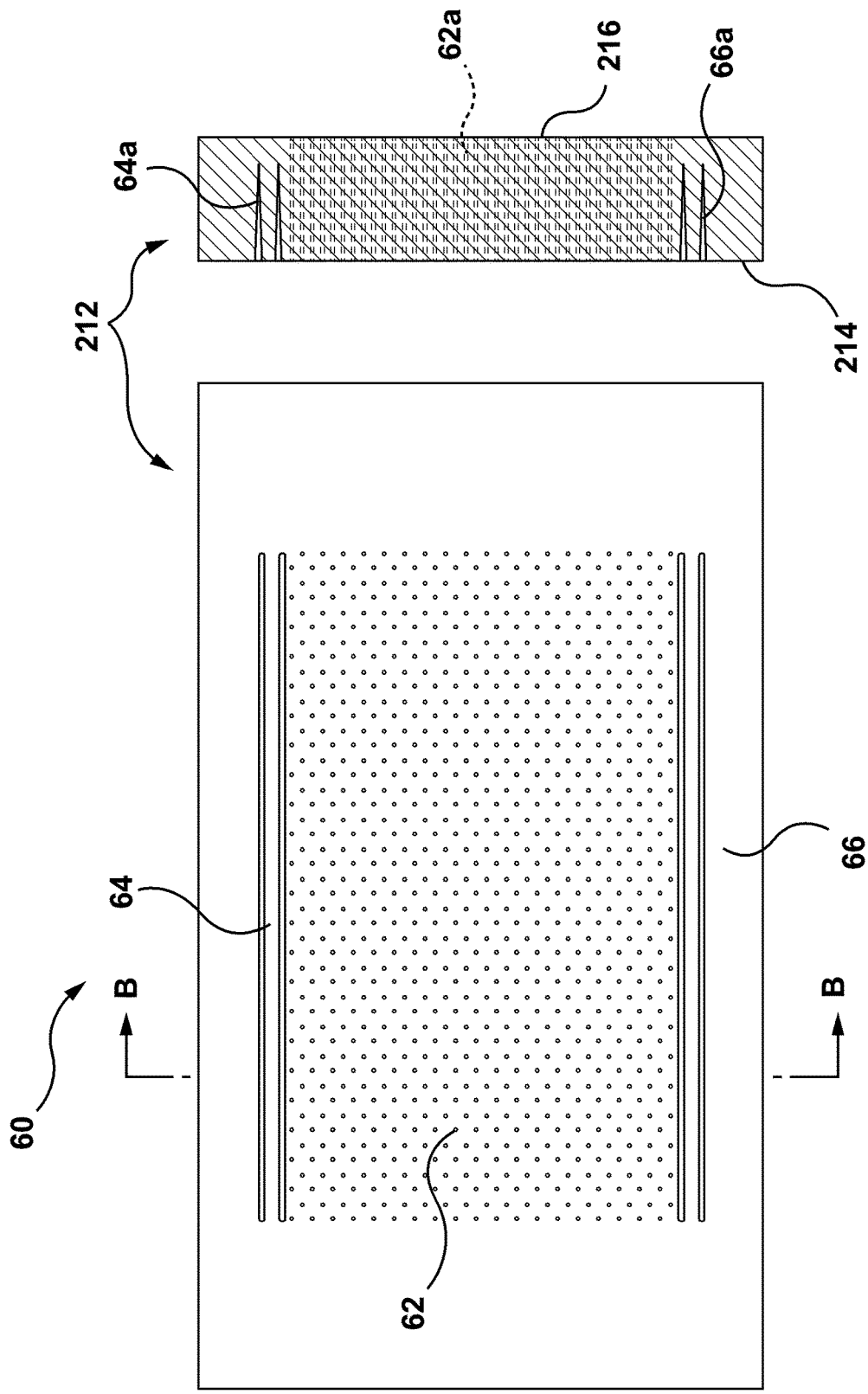

ATOMIZER CORES AND METHODS OF MANUFACTURING THE SAME

FIELD

The invention pertains generally to atomization applications. More specifically, the invention relates to atomizer cores for aerosol generating devices and methods of manufacturing atomizer cores.

BACKGROUND

Aerosol generating devices, also referred to as aerosol inhalers or vaporizers, include components for heating an aerosol precursor material to produce an aerosol for inhalation by a user. A problem with such components is that they may produce some harmful and potentially harmful constituents (HPHC). Also, prior known devices do not provide a desired level of control over dosage of aerosol.

There is a need for improved components for aerosol generating devices that address one or more problems with prior known devices such as those outlined above.

SUMMARY

In an aspect, there is provided an atomizer core, comprising: a core body having a first surface and a second surface, said core body including a substrate, a heater and an insulator disposed between said first surface and said second surface, said insulator being disposed between said substrate and said heater; and a plurality of channels extending between said first surface and said second surface for transferring an aerosol precursor from said first surface through said substrate, said insulator and said heater to said second surface, said heater being adapted to heat the aerosol precursor to form an aerosol at said second surface and said insulator being adapted to insulate said substrate at least partially from heat generated by said heater.

In another aspect, there is provided an atomizer core, comprising: a core body having a first surface and a second surface, said core body including a substrate formed from electrically conductive materials; and a plurality of channels extending between said first surface and said second surface for transferring an aerosol precursor from said first surface through said substrate to said second surface, said electrically conductive materials of said substrate being adapted to heat the aerosol precursor to form an aerosol at said second surface.

In another aspect, there is provided an atomizer core, comprising: a core body having a first surface and a second surface, said core body including a substrate formed from silicon; a plurality of channels extending between said first surface and said second surface for transferring an aerosol precursor from said first surface through said substrate to said second surface, said electrically conductive materials of said substrate being adapted to heat the aerosol precursor to form an aerosol at said second surface; wherein said substrate is treated with diffusion or ion implementation for conducting electricity and to generate heat for heating the aerosol source.

In another aspect, there is provided a method for manufacturing a substrate of an atomizer core, comprising: providing a glass substrate; treating the glass substrate at selected positions with laser to modify the properties of the glass substrate at the selected positions; and etching the glass substrate to form a plurality of the perforations at the selected positions.

In another aspect, there is provided a method for manufacturing a substrate of an atomizer core, comprising: providing a silicon substrate; photoresist patterning the silicon substrate at selected positions on a surface of the silicon substrate; and etching the silicon substrate to form a plurality of the perforations at the selected positions.

In another aspect, there is provided a method for manufacturing a substrate of an atomizer core, comprising: providing a substrate on a negative electrode of the electrolytic cell in a chemical solution; providing an electrode pin array as an anode of the electrolytic cell; applying a voltage between the perforation probe array and the negative electrode to corrode the substrate in the chemical solution; and generating perforations at selected points of the substrate.

In another aspect, the method is a porous anodic oxidation (PAO) method and the substrate is made of aluminum.

In another aspect, there is provided a substrate for an atomizer core, comprising: a first region comprising a plurality of perforations passing through a bottom surface and a top surface of the substrate, wherein aerosol source flows from the bottom surface to the top surface through the perforations when the atomizer cores in use; and one or more second regions adjacent to the first region, the one or more second regions comprising a plurality of blind perforations, wherein each of the blind perforations passes through the bottom surface of the substrate, extends at a depth toward the top surface, and is terminated at an end before the top surface. Alternatively, blind perforations open to top surface but terminate at an end before the bottom surface.

In another aspect, there is provided a substrate for an atomizer core, comprising: a first region comprising a plurality of perforations passing through a bottom surface and a top surface of the substrate, wherein aerosol source flows from the bottom surface to the top surface through the perforations when the atomizer cores in use; and one or more second regions adjacent to the first region, the one or more second regions comprising one or more blind lines, wherein each of the blind grooves passes through the bottom surface of the substrate, extends at a depth toward the top surface, and is terminated at an end before the top surface. Alternatively, blind lines open to top surface but terminate at an end before the bottom surface.

In another aspect, there is provided a substrate for an atomizer core, comprising: a first substrate portion and a second substrate portion, each of the first and second substrate portions having a plurality of through perforations; and a gap may or may not be formed between the first substrate portion and the second substrate portion.

BRIEF DESCRIPTION OF THE DRAWINGS

Reference will now be made, by way of examples, to the accompanying drawings which show example embodiments of the present application, and in which:

FIG. 7A is a top view of a substrate for an atomizer core, according to another embodiment of the present application;

FIG. 7B is a cross-sectional view of the substrate of FIG. 7A, alone line B-B;

Similar reference numerals may have been used in different FIGS. to denote similar components.

DESCRIPTION OF EXAMPLE EMBODIMENTS

Figure 1:
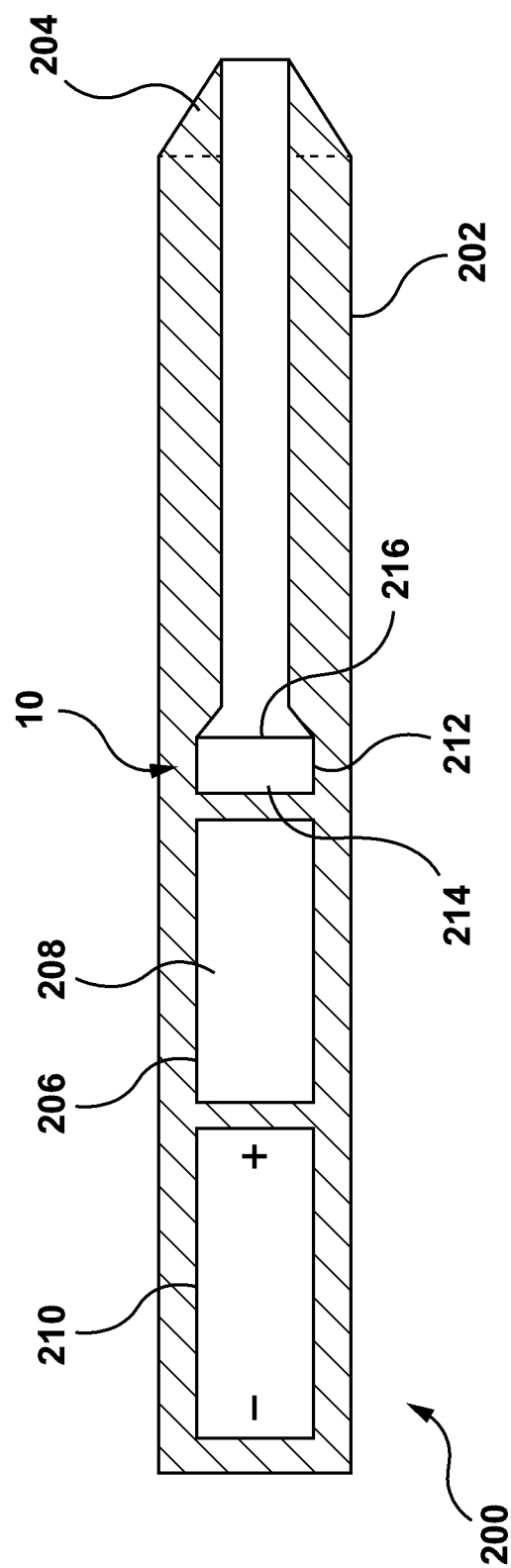
FIG. 1 is a schematic view of an aerosol generating device with an atomizer core according to an embodiment of the present invention.

FIG. 1 is a schematic view of an aerosol generating device 200 in accordance with an embodiment of the present invention. Aerosol generating device 200 includes a housing 202, a mouthpiece 204, a reservoir 206 for containing an aerosol precursor material 208 (also referred to as aerosol precursor or aerosol source herein), a power supply 210 and an atomizer core 10. Atomizer core 10 includes a core body 212 having a first surface 214 and a second surface 216. First surface 214 and second surface 216 are opposed to one another and parallel. First surface 214 is located proximate to reservoir 206 for receiving aerosol precursor 208. Second surface 216 is where aerosol is produced from aerosol precursor 208. First surface 214 is also referred to as a bottom surface herein with reference to atomizer core 10 or its components (such as substrate) and alternate embodiments. Similarly, second surface 216 is also referred to as a top surface herein with reference to atomizer core 10 or its components (such as substrate) and alternate embodiments.

Figure 2:
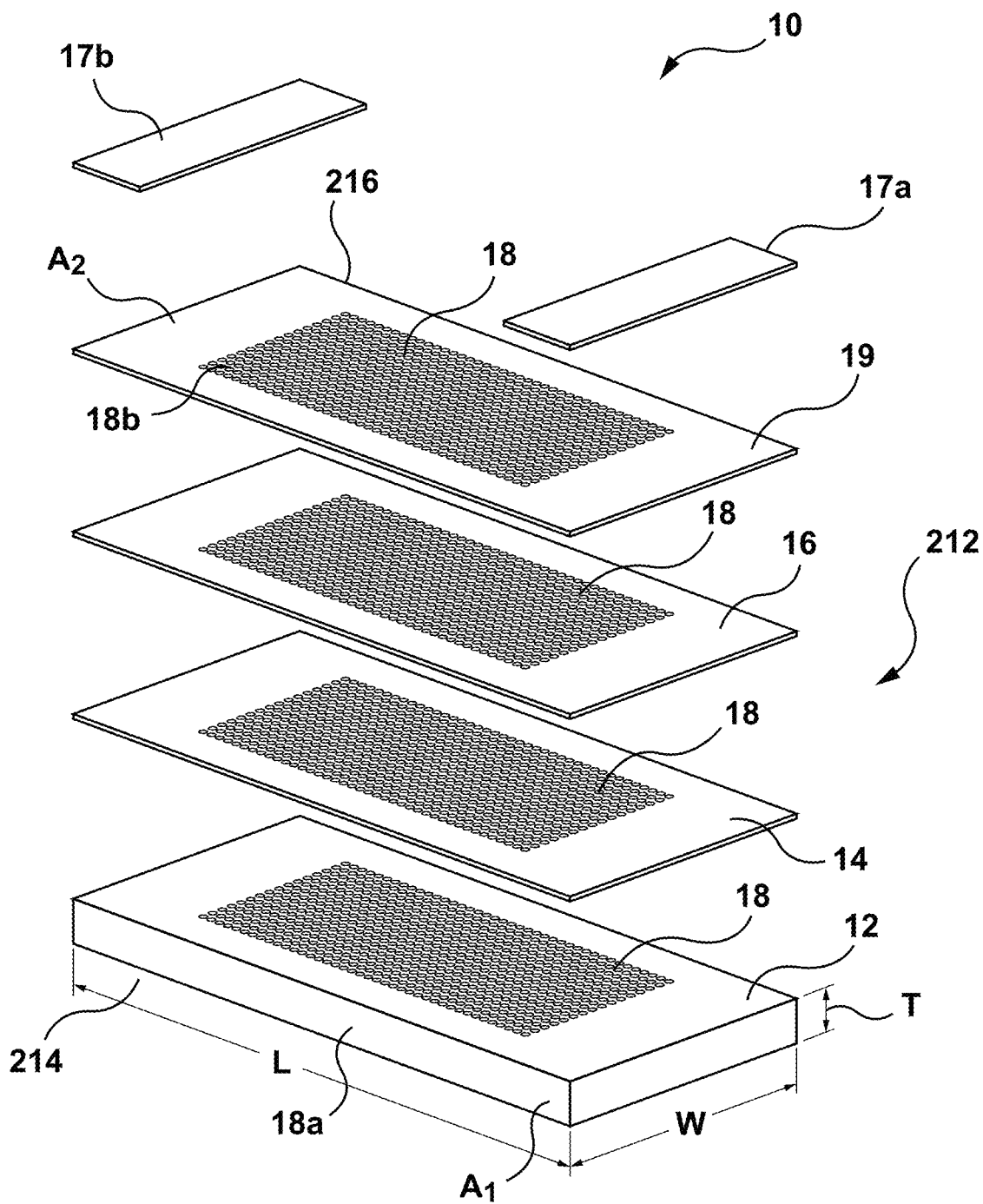
FIG. 2 is an exploded view of the atomizer core of FIG. 1.

Referring to FIG. 2, core body 212 includes a substrate 12, an insulator 14 and a heater 16. A plurality of perforations 18 (also referred to herein as channels or microchannels) are defined through core body 212 from first surface 214 to second surface 216 for transferring aerosol precursor 208 from first surface 214 through substrate 12, insulator 14 and heater 16 to second surface 216. As shown in FIG. 2 and other FIGS., the plurality of perforations 18 preferably have a uniform diameter and a uniform distribution or uniform spacing from adjacent perforations. Each perforation 18 includes a first opening 18a at first surface 214 and a second opening 18b at second surface 216. Perforations 18 are in fluid communication with aerosol precursor 208 with aerosol precursor 208 entering each perforation at first opening 18a and exiting each perforation 18 at second opening 18b where it changes to an aerosol. In this embodiment, first surface 214 and second surface 216 are each planar. First surface 214 has a first area A1 and second surface 216 has a second area A2. In this embodiment, core body 212 is box shaped with a length L, width W and uniform thickness T. Core body 212 may have other shapes as well such as shown with other embodiments.

Perforations 18 may be formed in one operation through core body 212, for example, by laser at the selected locations.

Perforations 18 may alternatively be initially formed in the substrate 12. The insulator 14 may be subsequently formed on the substrate 12, the heater 16 subsequently formed on the insulator 14, and the passive layer 19 or other layers may be subsequently formed on the heater 16 all using the process of thin film deposition. Since the thin film deposition process forms a film at an atomic level, such as at $10^{-10}$ meter level, and the perforations 18 on the substrate 12 have a much greater size, such as at $10^{-7}$ meter or larger level, insulator 14, heater 16, and passive layer 19 formed by the respective films will have substantially the same perforation sizes 18 as the substrate 12. Perforations 18 may alternatively be formed on insulator 14, heater 16, and passive layer 19 by screen printing on the substrate 12 with substantially the same perforation sizes 18 formed through all layers. Perforations 18 may be formed by other applicable technologies as well. The perforations 18 formed in each of the substrate 12, insulator 14, heater 16, and passive layer 19 collectively form perforations 18 extending between first surface 214 and second surface 216 of core body 212.

The diameter of perforations 18 may be from 15 nm to 250 microns, preferably 100 nm to 50 microns. In some examples, the diameter of the perforations in substrate 12, insulator 14, heater 16, passive layer 19 may be different. The diameter of the perforations 18 at the first surface 214 for example may be larger than, such as 500 micron (um) or greater, the size of the perforations 18 on the second surface 216 (in other words, perforations may taper from a larger diameter to a smaller diameter between first surface 214 and second surface 216).

The cross-sectional shape of the perforations 18 may be circular, oval, square, triangular, rectangular, or any other desired shapes. Preferably, the cross-sectional shape of all of the perforations 18 is uniform in the core body 212 for better dosage control.

Insulator 14 is disposed between substrate 12 and heater 16. Insulator 14 may comprise a layer or film that is deposited on substrate 12. Insulator 14 preferably has the same length L and width W of core body 212 and preferably has a uniform thickness which may be varied for different insulation materials and vaporing requirements. In some examples, insulator 14 can be made from low thermal conductive materials, such as $Al_2O_3$, $SiO_2$, $ZrO_2$, $HfO_2$, ZnO, and $TiO_2$.

Heater 16 may comprise a layer or film that is deposited on insulator 14. Heater 12 preferably has the same length L and width W of core body 212 and preferably has a uniform thickness in the range of, for example less than 20 microns. Heater 16 is configured to generate a desired amount of heat for heating or vaporizing the aerosol precursor 208 to generate an aerosol.

In some examples, after substrate 12 with perforations 18 is formed, the insulator 14 and heater 16 may be formed, for example, with metal or alloy thin films, conductive low-oxygen thin films, or coatings, or directly metal foil bonding. The heating performance of the heater 16 may be different by using materials with different resistance rate characteristics. In some examples, the heater 16 is made from bio-compatible metals or bio-compatible metals based alloys, or Ni—Cr based alloy. The bio-compatible metals may comprise Al, Ti, Ta, Zr, Pt, Au, Ag, Pd, Re, Yb, Y, Ce, La, Hf, Si, and alloys thereof, and medical stainless steel.

As such, with insulator 14, the heat loss due to the heat transfer from heater 16 to the substrate 12 is reduced or eliminated. Accordingly, with insulator 14, the atomizer core 10 is more efficient and quicker in heating the aerosol source to a desired temperature by heater 16 of the atomizer core 10. This helps improve the aerosol volume of the first puff and improves user experience. Accordingly, with the insulator 14, the vaping performance of the atomizer core 10, such as safety, taste, volume, vapor generation speed, is improved. By reducing heat loss, the insulator 14 also saves the power required by the heater 16 to heat the aerosol source, especially when the thermal conductivity of the substrate 12 is high.

In some examples, the insulator 14 can also be a buffer layer between the substrate 12 and the heater 16 to enhance the mechanical and thermal performances of the atomizer core 10 during the vaping.

In some examples, the atomizer core 10 may further include a passive layer 19 deposited on the exposed surface of the heater 16. The passive layer 19 protects the heater 16 from oxidization. In some examples, the passive layer 19 may be omitted, if the heater 16 is made from the material that is resistant to oxidization, such as Pd—Ag alloy, or Pt, Au, Pd, Re, metals, alloys based thereon, medical stainless steel, or Ni—Cr based alloy. In some examples, heater 16 made from metal or alloy films may include an additional passive layer 19 for protecting the oxidization of the heater 16 during the generation of aerosol.

In some examples, the atomizer core 10 may further include a pair of electrodes 17a and 17b for supplying power from power source 210, such as a battery, to heater 16. The electrodes 17a and 17b are made of biocompatible materials with good electrical conductivity, such as silver. The electrodes 17a and 17b are preferably in physical contact with heater 16. The atomizer core 10 can generate aerosol by heating aerosol source 208 by heater 16 to generate aerosol at the second surface 216 of the atomizer core 10. In some examples, the pair of electrodes 17a and 17b may be omitted from the atomizer core 10, if heater 16 is made from electrically conductive materials such as Ti or Ta or alloy foils of Ti or Ta, and the electrically conductive materials have sufficient thickness, such as over 20 um. If the passive layer 19 is included, the passive layer 19 is made from electrically conductive materials, such as gold or Au—Ag alloy.

Figure 3:
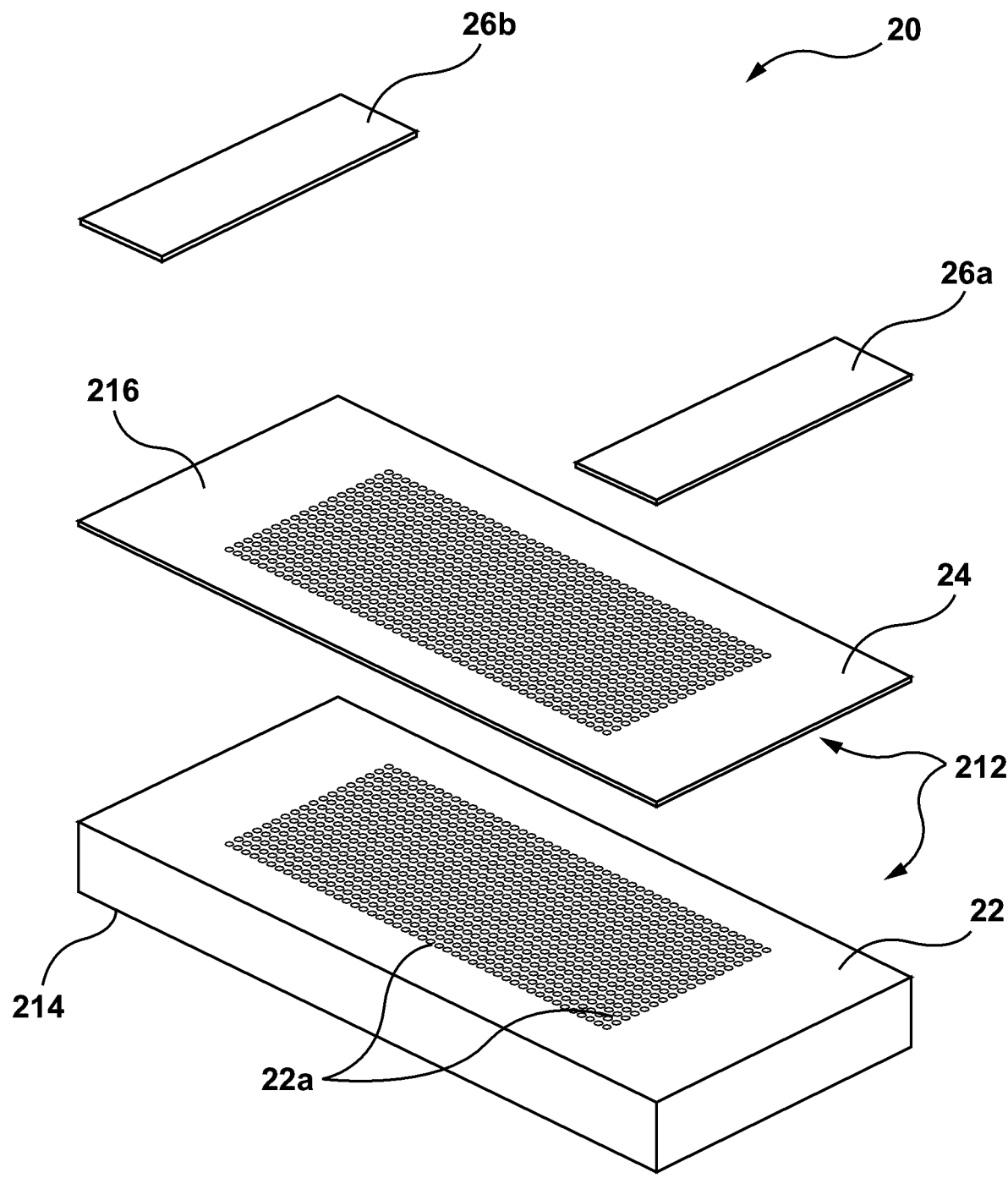
FIG. 3 is an exploded view of an atomizer core, according to another embodiment of the present application.

FIG. 3 illustrates another embodiment of an atomizer core 20. Similar reference numerals are used to refer to similar elements for the embodiments described herein. The atomizer core 20 includes a core body 212 having a first (or bottom) surface 214 and a second (or top) surface 216. Core body 212 includes a substrate 22 that is formed of an electrically conductive material. The substrate 22 has a plurality of microchannels formed by a plurality of perforations 22a. The plurality of perforations 22a allows an aerosol source to flow from the first surface 214 to the second surface 216 of the substrate 22. The substrate 22 is configured to generate heat for heating or vaporizing the aerosol source to generate aerosol. Substrate 22 is preferably made from SiC, metal or carbon-based ceramics, conductive silicon single crystals or polycrystals. With the electrically conductive materials, the substrate 22 can generate heat when the power is supplied to the substrate 22 from a power supply 210, such as a battery. As such, the substrate 22 can function as both a substrate and a heater. Accordingly, the atomizer core 20 has a simpler structure than existing atomizer cores.

In some examples, the substrate 22 may be made by a metal foil bonding process to form both the substrate and the heater. For example, Ti, Ta or other bio-metals or their alloys can be directly bonded to glass, crystals or ceramic substrates to form both the substrate and a conductive layer as the heater. In another example, Ti foil can be directly bonded to sapphire surface or quartz glass or other substrates. Perforations 22a may be formed in a similar manner as perforations 18 of atomizer core 10, as described above.

In some examples, the atomizer core 20 may further include a passive layer 24 placed on the top surface of the substrate 22. The passive layer 24 protects the substrate 22 from oxidization. The passive layer 24 may be made of materials that are oxidation resistant materials, such as $Al_2O_3$, $SiO_2$, $ZrO_2$, $HfO_2$, $TiO_2$ or $ZnO$. In some examples, if the material of the substrate 22 is also oxidation resistant, the passive layer 24 can be omitted from the atomizer core 20.

In some examples, the atomizer core 20 may further include a pair of electrodes 26a and 26b placed on the top surface of the substrate 22 or passive layer 24 for supplying power from a power source to the substrate 22 to generate heat. In either case, the electrodes 26a and 26b may be made of materials with good electrical conductivity, such as silver. The electrodes 26a and 26b are in electrical communication with the substrate 22. The pair of electrodes 26a and 26b may be omitted if the passive layer 24 is also electrically conductive.

In the example of FIG. 3, the passive layer 24 has the same perforation pattern as the substrate 22 and may be formed through the process of thin film deposition or other processes as described earlier. The passive layer 24 does not block the perforations 22a or microchannels of the substrate 22 and allows the aerosol source to flow to the top surface of the substrate 22.

Figure 4:
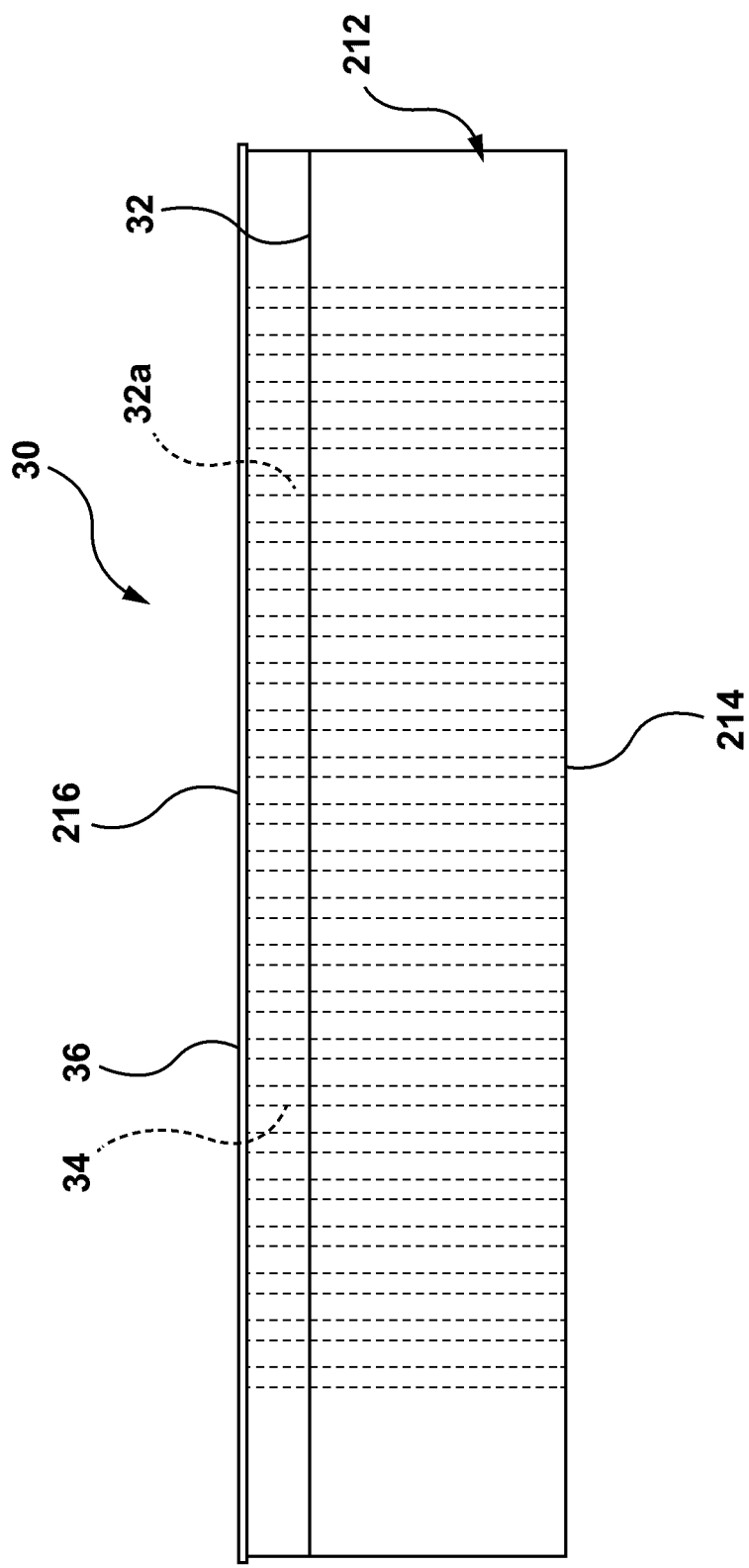
FIG. 4 is a cross-sectional view of an atomizer core, according to another embodiment of the present application.

FIG. 4 illustrates an atomizer core 30, according to another embodiment. The atomizer core 30 includes a core body 212 having a first surface 214 and a second surface 216. Core body 212 includes a substrate 32 formed of silicon. The core body 212 includes a plurality of microchannels formed by a plurality of perforations 32a. The plurality of perforations 32a allows an aerosol source to flow from the first surface 214 to the second surface 216 of the core body 212. Perforations 32a may be formed in a similar manner as perforations 18 of atomizer core 10, as described above.

In the example of FIG. 4, the silicon substrate 32 may be treated to be suitable for conducting electricity. For example, the silicon substrate 32 may be treated with diffusion or ion implementation to form a top layer 34. For example, the depth of diffusion or ion implementation may be less than 10 um. Ion implantation is a low-temperature process that includes the acceleration of ions of a particular element towards the silicon substrate 32, altering the chemical and physical properties of the silicon substrate 32. Ion implantation is isotropic and directional. Diffusion is used to introduce impurities into silicon substrate 32. Diffusion is isotropic and involves lateral diffusion. By treating the layer 34 with diffusion or ion implantation, the layer 34 provides low resistivity, for example with an electrical resistance of $10^{-1}$-$10^{-5}$ Ω/m. The low resistivity of the treated layer 34 allows the layer 34 to conduct electricity. Accordingly, the treated layer 34 can function as a heater. When the power is supplied to the layer 34, the treated layer 34 can generate heat for generating aerosol from the aerosol source spread on the surface 34. In an alternative embodiment, the silicon substrate 32 may be further treated with diffusion or ion implementation to form a SiO2 insulator layer between substrate 32 and top layer 34.

Figure 5:
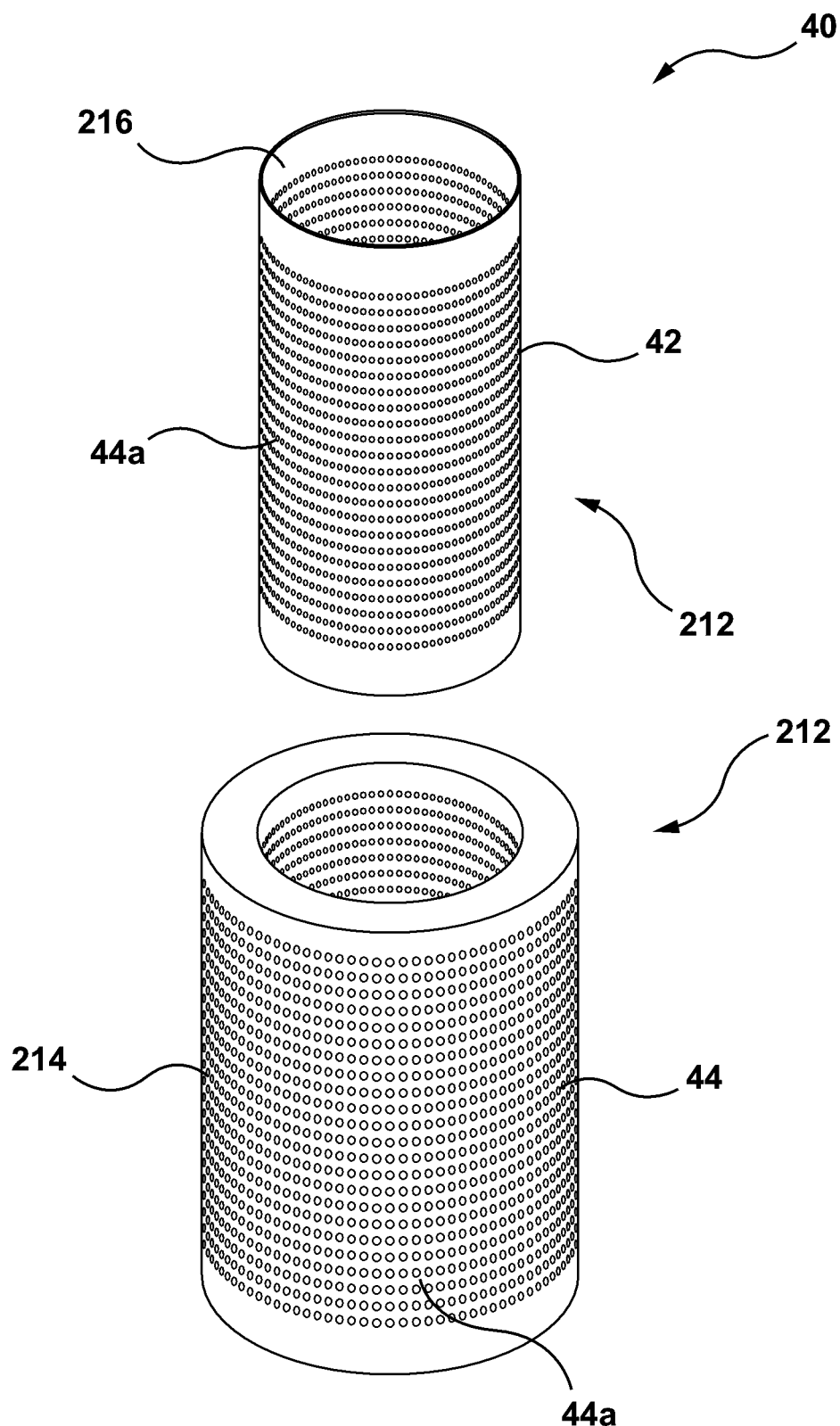
FIG. 5 is an exploded view of an atomizer core, according to another embodiment of the present application.

FIG. 5 illustrates an atomizer core 40, according to another embodiment of the present application. In the example of FIG. 5, the atomizer core comprises a core body 212 having a first surface 214 and a second surface 216. Core body 212 includes a tubular substrate 44 and a tubular heater 42 for covering the inner surface of the tubular substrate 44. An insulator may be added between the substrate 44 and the heater 42. A passive layer may also be added to the heater 42.

The core body 212 includes a plurality of microchannels formed by a plurality of perforations 44a. The plurality of perforations 44a allows an aerosol source to flow from an outer surface of the tubular substrate 44 to the tubular heater 42 at the inner surface of the tubular substrate 44 for generating aerosol. Perforations 44a may be formed in a similar manner as perforations 18 of atomizer core 10, as described above.

In some examples, if the aerosol source is located at the outer surface of the tubular substrate 44, the plurality of perforations 44a allows the aerosol source to flow from the outer surface to the heater 42 at the inner surface of the tubular substrate 44 for generating aerosol. In some examples, if the aerosol source is located at the inner surface of the tubular substrate 44, the plurality of perforations 44a allow the aerosol source to be flowed from the inner surface to the heater 42 located at the outer surface of the tubular substrate 44 for generating aerosol.

The tubular heater 42 may be made from the same material as the heater 16 in the example of FIGS. 2 and 3. The tubular substrate 44 may be made from the materials of the substrate 22 in the example of FIG. 4 or the silicon substrate layer 34 treated with diffusion or ion implantation in the example of FIG. 4. In this case, the tubular heater 42 can be omitted. Either the inner surface or outer surface of the tubular substrate 44 may be selected to generate heat, when the power is supplied to the tubular substrate 44, for generating aerosol from the aerosol source at the tubular substrate 44.

In the examples of atomizer cores 10, 20, 30 and 40 above, the microchannels formed by perforations of the core body 212 may be substantially perpendicular to the first and second surfaces 214 and 216 of the core body 212 or form any angle between the microchannels and the first and second surfaces of the core body 212.

Figures 6A, 6B:
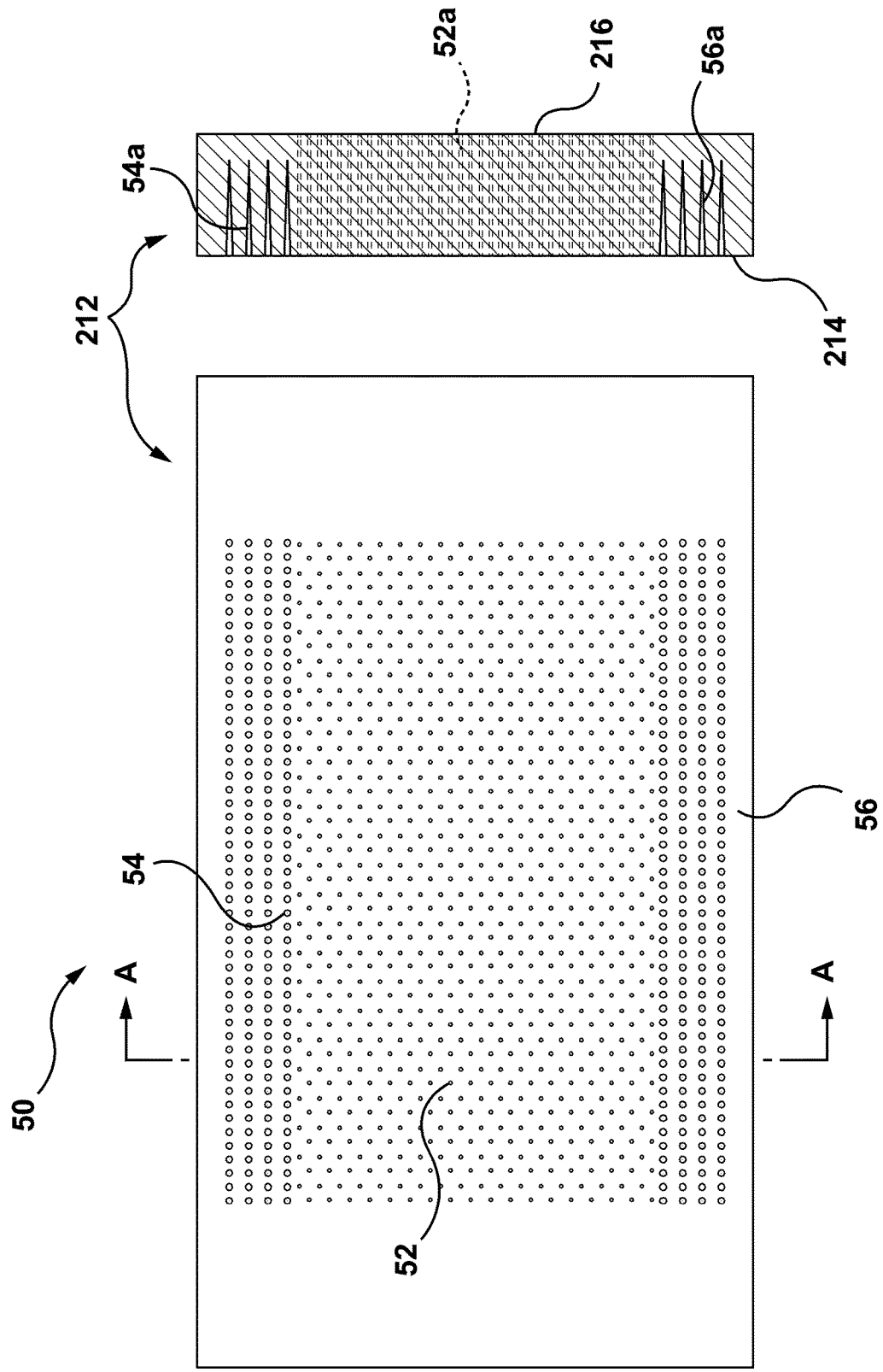
FIG. 6A is a top view of a substrate for an atomizer core, according to another embodiment of the present application.
FIG. 6B is a cross-sectional view of the substrate of FIG. 6A, along line A-A.

FIGS. 6A and 6B illustrates a substrate 50, according to another embodiment of the present application. In the example of FIGS. 6A and 6B, the substrate 50 may include a first region 52 and second regions 54 and 56. Each second region may be adjacent to the first region 52.

As illustrated in the example of FIG. 6A, the first region 52 comprises a plurality of perforations 52a. As illustrated in FIG. 6B, each perforation 52a passes through the bottom surface 214 and top surface 216 of the substrate 50 and forms a microchannel. In the example of substrate 50, perforations 52a are substantially straight and substantially perpendicular to the top and bottom surfaces 214, 216 of the substrate 50. The perforations 52a may also be configured to be substantially straight but form any angle with the top surface 216 or bottom surface 214 of the substrate 50. When the substrate 50 is in use as an atomizer core, the aerosol source is flowed from the bottom surface 214 to the top surface 216 through the perforations 52a.

The second regions 54 and 56 each comprise a plurality of blind perforations 54a or 56a. As illustrated in FIG. 6B, each of the blind perforations 54a and 56a passes through the bottom surface 214 of the substrate 50. Each of the blind perforations 54a and 56a extends at a depth toward the top surface 216 and is terminated at an end before the perforation reaches the top surface 216. The depth is less than the thickness of the substrate 50. As such, when the substrate 50 is in use as an atomizer core, the aerosol source does not flow from the bottom surface 214 to the top surface 216 in regions 54 and 56 but stops at the end of the perforations 54a or 56a, or at some point between the bottom surface 214 and the end of the perforations 54a or 56a. Therefore, when an atomizer core comprising the substrate 50 is in use, the aerosol source may be stored in the blind perforations 54a and 56a during puffing. The blind perforations 54a and 56a may also store condensed residual aerosol after puffing. In contrast, the aerosol source in the first region 52 simply passes through the microchannels defined by the perforations 52a of the substrate 50 to the top surface 216 of the atomizer core for generating aerosol.

In another example, some or all of the blind perforations 54a and 56a may pass through the top surface 216 of the substrate 50. The blind perforations 54a and 56a extend at a depth toward the bottom surface 214 and are terminated at an end before the blind perforation reaches the bottom surface 214. The depth is less than the thickness of the substrate 50.

The second region 54 or 56 formed by the blind perforations 54a and 56a may have the same, shorter or longer length than the length of the first region 52.

In an example, each of the blind perforations 54a and 56a may have a depth of 700 um from the bottom surface 214, and a diameter of 30 um. Each of the perforations 52a may have a depth of 1 mm from the bottom surface 214 to the top surface 216. The total number of the blind perforations 54a and 56a may be over several hundreds or thousands, such as 396 blind perforations. The total area of the second region may be around 700 um$^2$. The total area of the substrate 50 may be around 28,000 um$^2$; and the total volume of the substrate may be over 195 million um$^3$.

The perforations array may be in other shapes for different functions.

In the example of FIG. 6A, the first region 52 is substantially rectangular and thus have upper, lower, left and right sides. The substrate 50 includes second regions 54 adjacent to the upper side of the first region 52, and second regions 56 adjacent to a lower side of the first region 52. The substrate 50 may also include one or more additional second regions at the left side and/or right side of the first region 52.

The first region 52 may have any desired shapes, such as a circular shape or other polygonal shapes. The substrate 50 may include one or more second regions adjacent to one or more sides of the first region 52. For example, if the first region 52 has a circular shape, the second region may comprise a plurality of blind perforations 54a and 56a forming one or more arcs adjacent to the circumference of the first region 52, or forming one or more complete rings surrounding the first region 52.

FIGS. 7A and 7B illustrate another example of a substrate 60. The substrate 60 may include a first region 62 and one or more second regions 64 and 66. Each second region may be adjacent to one side of the first region 62.

As illustrated in the example of FIG. 7A, the first region 52 comprises a plurality of perforations 62a. The perforations 62a are the same as the perforations 52a as described in FIGS. 6A and 6B.

The second regions 64 and 66 each comprise one or more blind lines 64a and 66a. In the example of FIGS. 7A and 7B, each of the second regions 64 and 66 comprises two blind lines. As illustrated in FIG. 7B, each of the blind lines 64a and 66a may be a substantially straight blind line adjacent to one side of the first region 62. Each blind line 64a or 66a may also have other desire shapes, such as a waved line. Each of the blind lines may be formed at the bottom surface 214 of the substrate 60 and extended into the substrate 60 to a desired depth. The depth is less than the thickness of the substrate 60. Each of the blind lines 64a and 66a is extended into the substrate at an end before it reaches the top surface 216 of the substrate 60. In the example of FIG. 7B, the aperture of the blind line at the bottom surface 214 may be wider than the end. In some examples, the aperture of the blind line at the bottom surface 214 may be the same or narrower than the end.

In another example, one or more of the blind lines may be formed at the top surface 216 of the substrate 60 and extend into the substrate 60 toward the bottom surface 214 to a desired depth. The depth is less than the thickness of the substrate 60.

The one or more of the second regions 64 and 66 formed by the blind lines 64a and 66a may have the same, shorter or longer length than the length of the first region 62.

Similar to the blind perforations 54a and 56a in FIGS. 6A and 6B, when the substrate 60 is in use as an atomizer core, the aerosol source in the blind lines 64a and 66a does not flow from the bottom surface 214 to the top surface 216 of the substrate 60. The aerosol source stops at the end of the blind lines 64a or 66a, or at some point between the bottom surface 214 and the end of the blind lines 64a or 66a. Therefore, when an atomizer core comprising the substrate 60 is in use, the aerosol source may be stored in the blind lines 64a and 66a during puffing. The blind lines 54a and 56a may also store condensed aerosol source after puffing.

In the example of FIG. 7A, the first region 62 is substantially rectangular and thus have upper, lower, left and right sides. The substrate 60 includes two second regions 64 and 66 at the upper side and lower side of the first region 62. The substrate 60 may also include one or more additional second regions at the left side and/or right side of the first region 62.

The first region 62 may have any desired shape, such as a circular shape or other polygonal shapes. The substrate 60 may include one or more second regions adjacent to one or more sides of the first region 62. For example, if the first region 62 has a circular shape, the second region may comprise one or more arcs adjacent to the circumference of the first region 52, or one or more complete circles surrounding the first region 62.

In an example, each of the blind lines 64a and 66a may have a depth of 700 um from the bottom surface 214. The depth of the through perforations 62a is around 1 mm. Each of the blind lines 64a and 66a may be a straight line with a length over 5000 um; the total number of the blind lines 64a and 66a may be two on the upper side and lower side of the first region 62. The width of the aperture on the bottom surface may be around 30 um. The total area of the blind lines may be over 150,000 um$^2$. The total area of the substrate 60 may be around 630,000 um$^2$; and the total volume of the substrate may be over 400 million um$^3$.

As described above, when the atomizer core is powered on, the heater becomes heated for vaporizing the aerosol source. The heat transferring from the heated area to the edge of the substrate is reduced. As such, more energy is available to vaporize the aerosol source to generate more aerosol with the same amount of power.

With less heat being transferred to the edge of the substrate 50 at the second regions 54 and 56, and to the edge of the substrate 60 at the second regions 64 and 66, the heat generated by the heater of the atomizer core is concentrated at the first regions 52 and 62. As such, each of the first regions 52 and 62 has a higher concentrated energy. Accordingly, with substrates 50 or 60, the aerosol source becomes quicker and easier to be vaporized. As well, this allows power saving, since less power of the aerosol generating device comprising substrate 50 or 60 may be consumed to reach the desired temperature at the first region 52 or 62.

The lower temperature at the top surface 216 of the second regions 54 and 56, or 64 and 66, allows better sealing performance of the atomizer core comprising the substrate 50 or 60 with the materials surrounding the atomizer core, such as plastic. For example, the physical characteristics and mechanical strength of surrounding materials are less likely to be damaged or deteriorated by high temperature of the first region of substrate 50 or 60.

The substrates 50 and 60 may be the substrate of atomizer cores 10, 30 and 40 as described above. The substrates 50 and 60 may also be the substrate of any atomizer core for generating aerosol from an aerosol source.

Figure 8A:
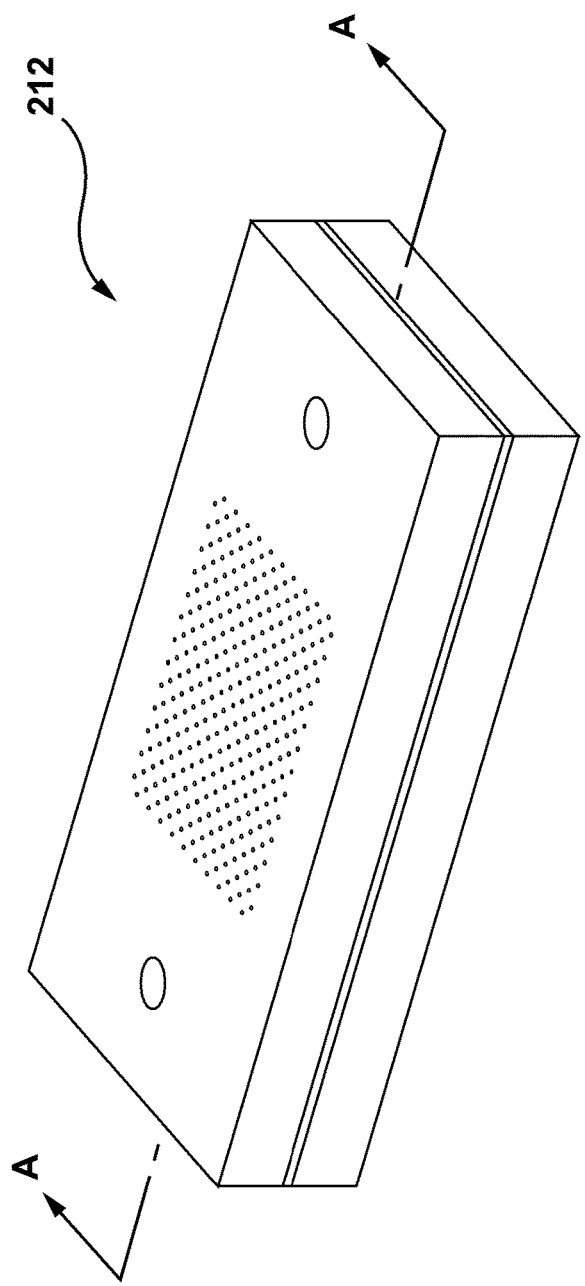
FIG. 8A is a perspective view of a substrate for an atomizer core, according to another embodiment of the present application.
Figure 8B:
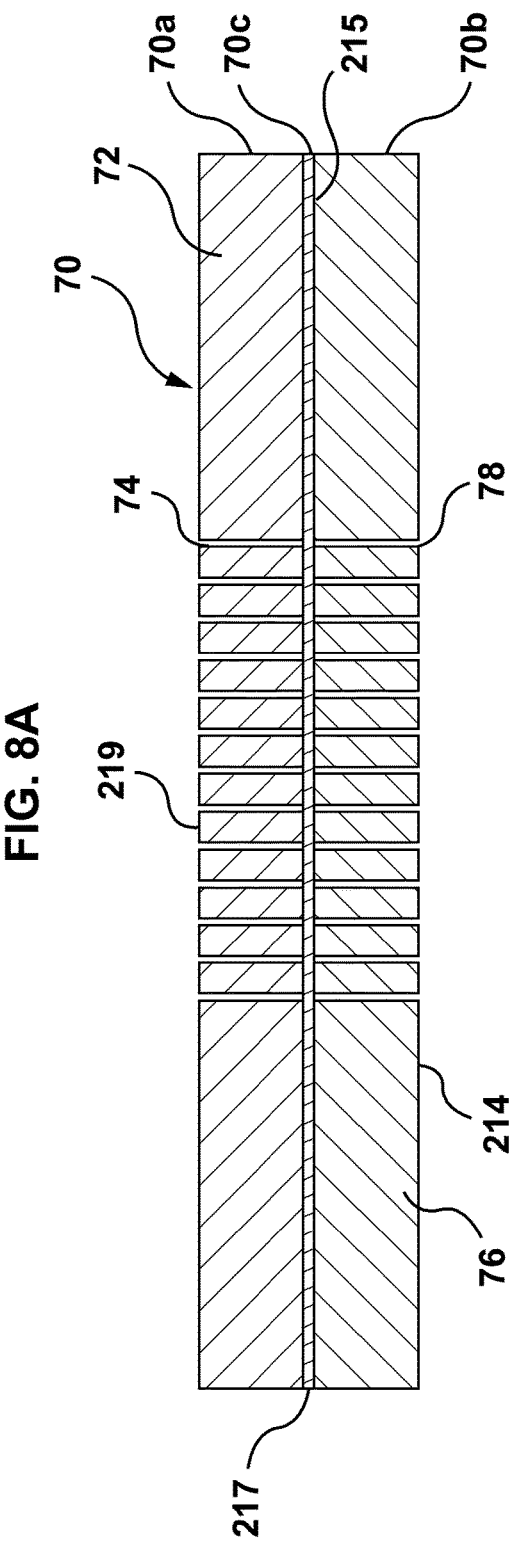
FIG. 8B is a cross-sectional view of the substrate shown in FIG. 8A as viewed along lines A-A.
Figure 8C:
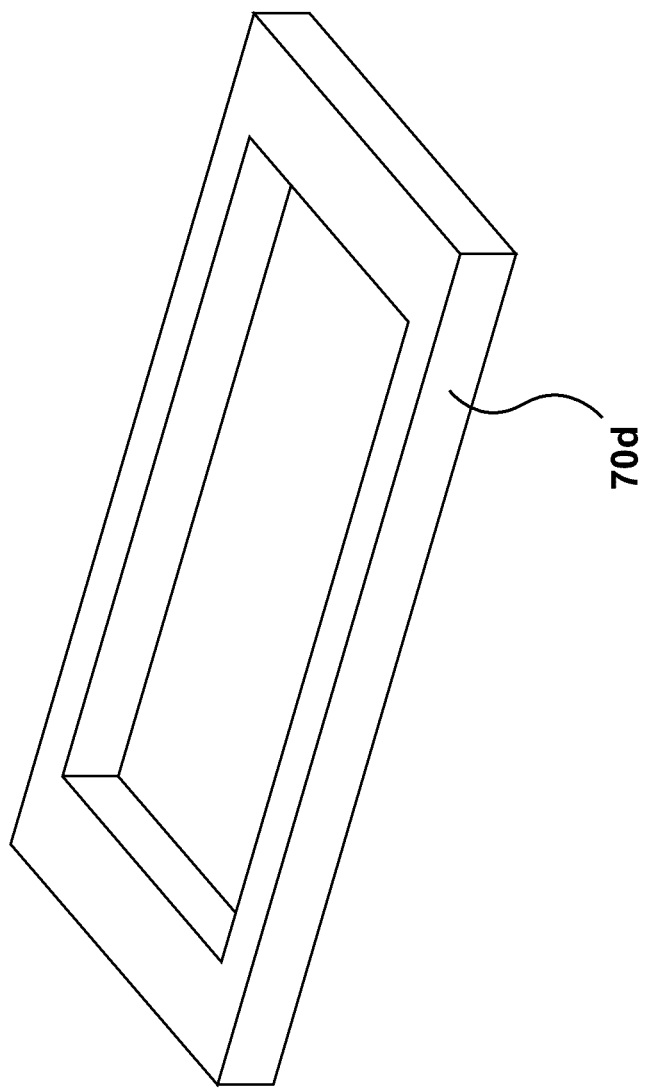
FIG. 8C is a perspective view of a pad used with the substrate shown in FIG. 8A
Figure 9:
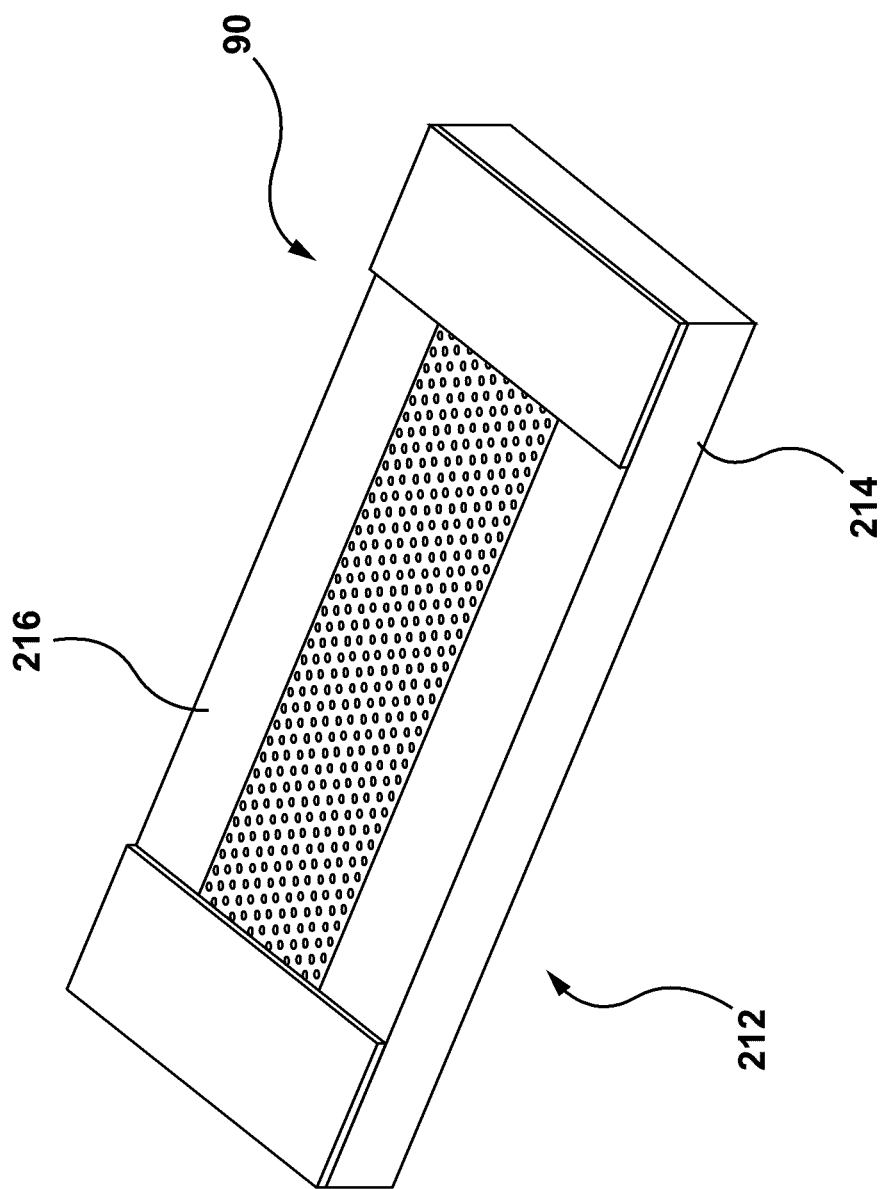
FIG. 9 is a schematic view of an atomizer core, according to another embodiment of the present application.
Figure 10A:
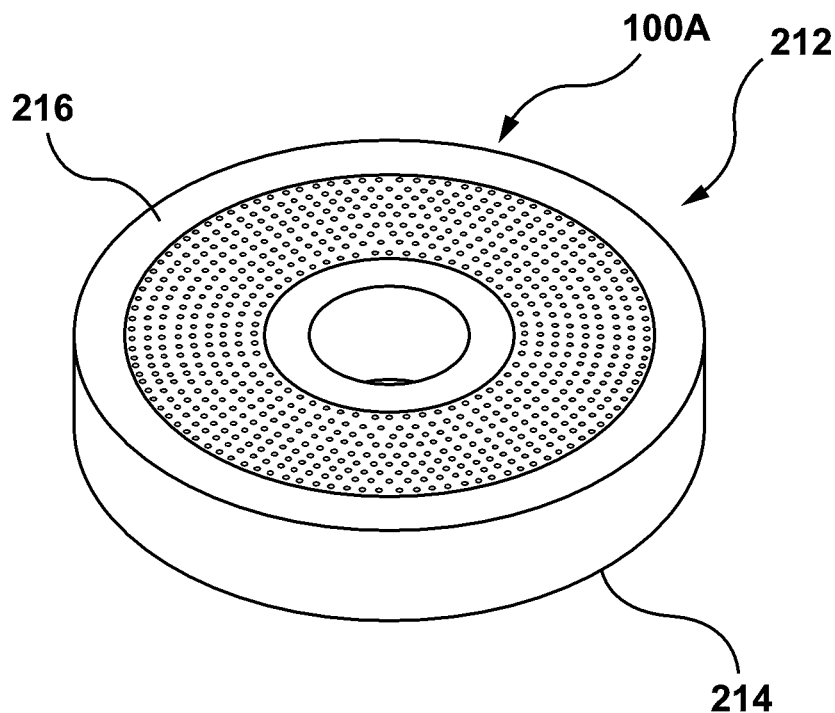
FIGS. 10A-10B are schematic views of two atomizer cores, according to another embodiment of the present application.
Figure 10B:
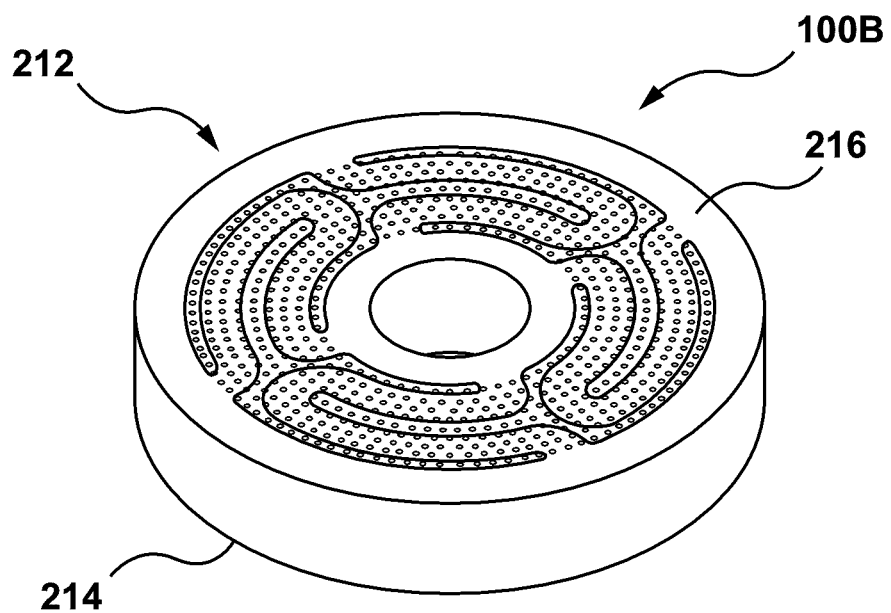
Figure 11A:
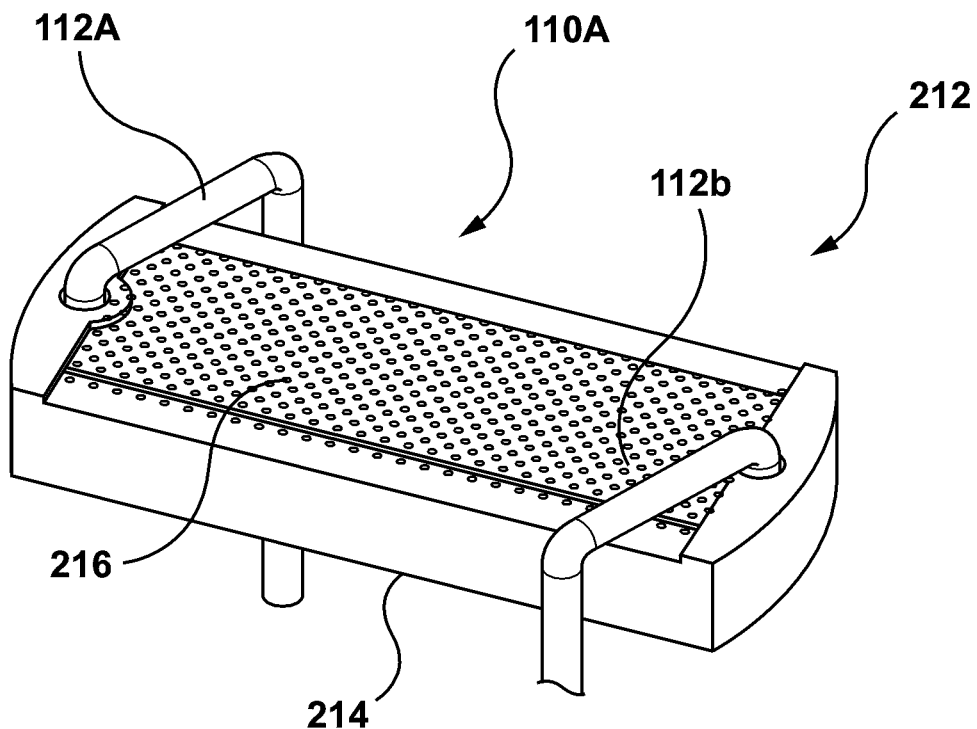
FIGS. 11A-11B are schematic views of two atomizer cores, according to another embodiment of the present application.
Figure 11B:
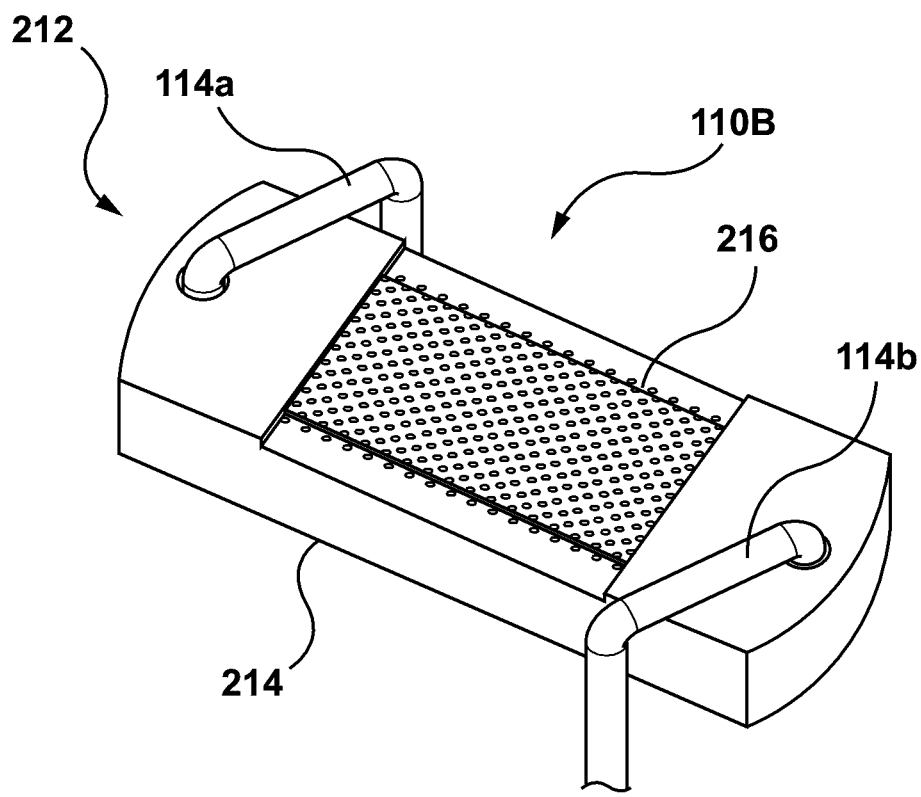
Figure 12:
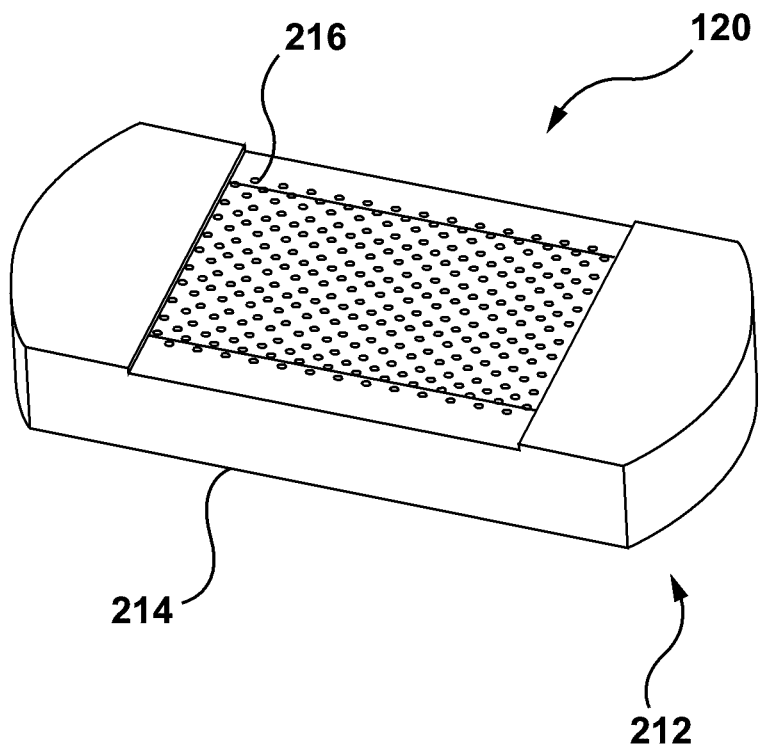
FIG. 12 is a schematic view of an atomizer core, according to another embodiment of the present application.
Figure 13:
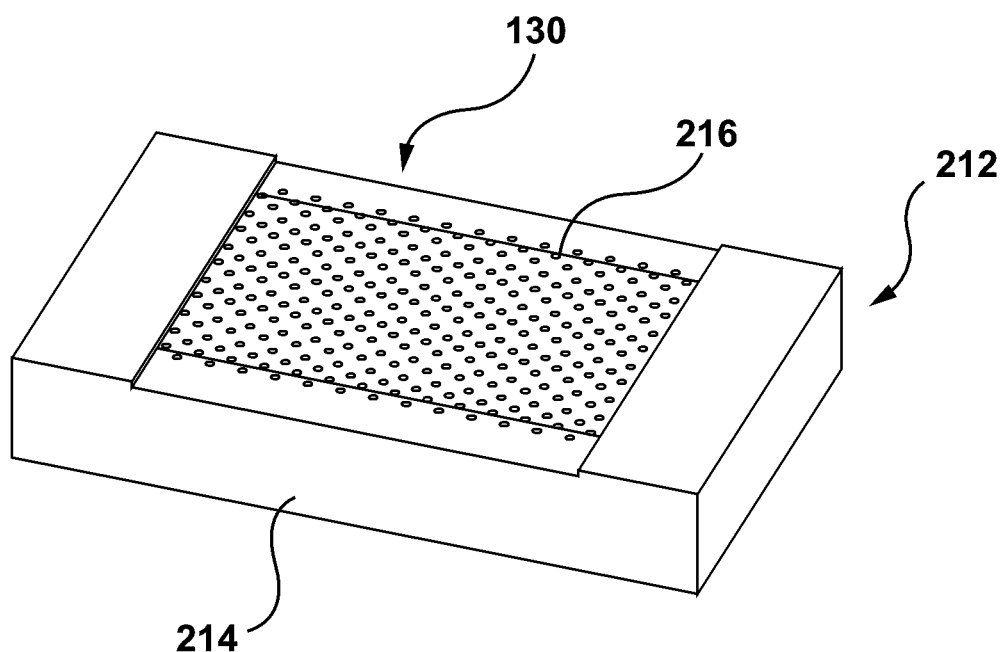
FIG. 13 is a schematic view of an atomizer core, according to another embodiment of the present application.

FIGS. 8A-8C illustrate a substrate 70 according to another embodiment. The substrate 70 comprises a first substrate portion 70a and a second substrate portion 70b, and a layer 70c between the first substrate portion 70a and the second substrate portion 70b. The layer 70c forms an aerosol source film between the first substrate portion 70a and the second substrate portion 70b.

The first substrate portion 70a has a plurality of through perforations 74. The second substrate portion 70b has a plurality of through perforations 78. Each of the through perforations 74 and 78 forms a microchannel. The microchannels formed by through perforations 78 allow the aerosol source to flow from the bottom surface 214 of the second substrate portion 70b to a top surface 215 of the second substrate portion 70b. The aerosol source may then reach the layer 70c. The microchannels formed by through perforations 74 allow the aerosol source to flow from the layer 70c to a bottom surface 217 of the first substrate portion 70a and then to a top surface 219 of the first substrate portion 70a for generating aerosol at the top surface of an atomizer core when the atomizer core is in use for vaping.

In the example of FIGS. 8A-8C, the through perforations 78 generally align with the through perforations 74. In some examples, the through perforations 78 may be misaligned with the through perforations 74. In either case, the aerosol source from the through perforations 78 first flows to the layer 70c and forms an aerosol source film at the layer 70c between the first substrate portion 70a and the second substrate portion 70b. The aerosol source may then flow from the layer 70c to the through perforations 74 for generating aerosol at a top surface of an atomizer core comprising the substrate 70.

For example, the atomizer core may be atomizer cores 10, 20, 30 and as described above, or any atomizer core comprising the substrate 70.

In some examples, the layer 70c may be materials that absorb the aerosol source, such as cotton and hemp. In some examples, the layer 70c may be a free air space defined between the first substrate portion 70a and the second substrate portion 70b. For example, the air space may be formed by a pad 70d at each of the left and right ends of the second substrate portion 70b. The pad 70d may be formed by alumina foil, or any other suitable materials.

With the layer 70c, the temperature difference between the top surface 219 of the substrate 70 (the top surface 219 of the first substrate portion and the bottom surface 214 of the substrate 70 (the bottom surface 214 of second substrate portion 70b) is substantially increased. In an example, each of the first substrate portion 70a and the second substrate portion 70b is 0.5 mm sapphire, and the layer 70c is a 0.1 mm aerosol source layer. The temperature difference between the top surface 219 and the bottom surface 214 of the substrate 70 is about 72K. In contrast, the temperature difference between the top surface 219 and the bottom surface 214 of the substrate 70 with a 1 mm sapphire is around 8K, and the temperature different between the top surface 219 and the bottom surface 214 of the substrate 70 with a 0.5 mm sapphire is around 4K.

As such, with the layer 70c that causes the temperature difference between the top surface 219 of the substrate 70 and the bottom surface 214 of the substrate 70 substantially increased, the heat transfer from the top surface 219 of the substrate 70 to the bottom surface 214 of the substrate 70 is significantly reduced. In other words, the heat loss of the substrate 70 has been greatly reduced. Therefore, due to the reduced heat loss, atomizer core comprising the substrate 70 may have a better vaporizing performance and save more power of the battery of an aerosol generating device using the atomizer core, reduce the risk of leaking and clogging of aerosol source in the microchannels. Furthermore, temperature reducing can also improve the uniform vaping, that means, reduce the opportunity for low boiling temperature ingredient vaping first. Therefore, the atomizer core with substrate 70 has an improved puffing performance.

In the examples of atomizer cores 10, 20, 30 and 40, vaping performance of the atomizer core may be further improved by modifying the surface characteristics of the second surface 216 of the atomizer core. For example, E-cig, WO3/ZrO$_2$, WO3/TiO2, SiO2/Al2O3, TiO2 surfaces may perform as a catalyst to enhance the reaction of Vegetable Glycerin (VG) to become acrylic aldehyde or Allyl alcohol, both are HPHC in the aerosol. The second surface 216 may be modified to raise the reaction energy barrier to avoid such chemical reaction and make the vaping only a physical, but not chemical, phenomenon. For example, a carbon layer may be used as a vaping interface to raise the reaction energy barrier. The modified surface character of the second surface 216 can improve the liquid flow in the microchannel and the fluid distribution or spreading on the second surface 216 of the atomizer core. As discussed above, the second surface 216 of the core body 212 may be the top surface of the heater, or if the atomizer core includes a passive layer, the top surface of the passive layer, or other functional layer(s) on the passive layer. The surface modification can control the wetting performances between the aerosol source and the second surface 216, and between the aerosol source and the microchannel surfaces.

For example, the second surface 216 of the core body of the atomizer core can be formed with a gold or silver thin film, which can easily wet THC oil which means THC oil can be evenly distributed on the second surface 216. A liquid is wet to the surface if the contact angle is less than 90 degrees. Wetting is the ability of a liquid to maintain contact with a solid surface, resulting from intermolecular interactions when the two are brought together. The degree of wetting (wettability) is determined by a force balance between adhesive and cohesive forces. Wetting deals with three phases of matter: gas, liquid, and solid. The second surface 216 of the atomizer core may also be small silicone molecular top surface, which can easily unwet E-juice; and ion or plasma treated top surface can also change the wetting performance of an atomizer core. The wet extent can be controlled with the duration and strength of power for treating the top surface. For example, plasma treated TiO$_2$ surface can have a continuous wetting performance from fully unwet to fully wet with water with plasma time and strength.

In some examples, the second surface 216 of an atomizer core 10, 20, and 40 can have an anti-catalyst layer by increasing the energy barrier of the thermal decomposition reaction. For example, in FIG. 4, an anti-catalyst layer 36 is formed on the second surface 216. This provides consistent aerosol generating performances in the same manner as physical aerosol generation. The energy barrier can be raised to some level for thermal decomposition or pyrolysis reaction control. Harmful and potential harmful constituents (HPHC) in aerosol result from the thermal decomposition or pyrolysis reaction of organic ingredients or other chemical reactions between the ingredients in the aerosol source. The activation energy of thermal decomposition is varied with the different aerosol generating interfaces. Increasing energy barrier to chemical reaction can prevent thermal decomposition of organic ingredients. For example, energy barrier can be increased by using gold surface. For example, if the second surface 216 of an atomizer core is WO3/ZrO2, WO3/TiO2, SiO2/Al2O3, TiO2 surface, Vegetable Glycerin (VG) can easily form acrylic aldehyde or Allyl alcohol during vaping. Carbon layer may be used for this purpose.

An atomizer core may have different aerosol generating performance with its second surface 216 facing different directions. The atomizer core may be mounted to an aerosol device with the second surface 216 facing upward toward the outlet of the aerosol device. The aerosol generated at the second surface 216 of the atomizer core is ascended and exits by a first path along the tube channel toward the outlet of the atomizer core.

An atomizer core may also be mounted to an aerosol device with the second surface 216 facing downward at a direction opposite to the outlet of the aerosol device. The aerosol generated at the second surface 216 of the atomizer core ascends from the sides of the atomizer core by additional second paths around the atomizer core from the second surface 216, and then exits with the first path as the heating surface facing upward along in the tube channel toward the outlet of the aerosol device.

Therefore, the total aerosol path of the second path and the first path with the second surface 216 facing at a direction opposite to the outlet of the aerosol device is longer than the first path with the second surface 216 facing toward the outlet of the aerosol device. The additional second path causes additional heat loss of the aerosol. As such, due to the shorter distance between the second surface 216 of the atomization core and the outlet with the second surface 216 facing toward the outlet of the aerosol device, the temperature of aerosol at the outlet of the aerosol generating device is higher than the temperature of aerosol at the outlet of the aerosol generating device with the second surface 216 facing at a direction opposite to the outlet of the aerosol device. The user has the option to select the aerosol generating device with the second surface 216 of the atomizer core facing either toward or away from outlet, depending on personal preferences and may experience better taste of the aerosol with higher aerosol temperature, and thus have a better user experience.

In an aerosol generating process at an atomizer core, in additional to providing microchannels to allow the aerosol source to flow through, the substrates in the present application also thermally insulate the aerosol source from the heater of the atomizer core. The atomizer core only heats the aerosol source flowed from the aerosol source container to the second surface 216 of the atomizer core, but not the aerosol source in the container. As such, the atomizer core keeps the taste of the aerosol from first puff to the last puff consistent and keeps the aerosol composition substantially the same in puffing.

In an aerosol generating process, an atomizer core may comprise one or more layers, similar to atomizer cores 10, 20, 30 and 40. When the substrate is in fluid communication with the aerosol source, the aerosol source may saturate microchannels prior to the second surface 216 of the atomizer core being heated. In some examples, the passive layer covering the heater may have a configured amount of wetting, so that the aerosol source on the second surface 216 of the passive layer may be controlled to have a desired spreading pattern. When the power is supplied to the heater for heating the atomizer core, the heated atomizer core reduces the viscosity of the aerosol source in the microchannels and increases flow-through rate of the aerosol source in the microchannels. Aerosol is generated from the second surface 216 of the atomizer core, such as the passive layer, and is carried to the user by airflow. Due to the low thermal conductivity co-efficiency of the insulator both the heated atomizer core and the aerosol sources contained in an aerosol generating device become cool as soon as the power supply is stopped. This reduces the flow-through rate of the aerosol source in the microchannels and then reduces the likelihood of the aerosol source leaking.

FIG. 9 illustrates the atomizer core 90 with a substantially rectangular shape. The atomizer core 90 may be mounted in an aerosol device with the second surface 216 of the atomizer core 80 facing upward (in other words, facing towards the outlet or mouthpiece). The atomizer core 90 may also be mounted to an aerosol device with the second surface 216 of the atomizer core 90 facing downward (in other words, facing away from the outlet or mouthpiece).

FIGS. 10A-10B are two exemplary embodiments of atomizer cores 100A (FIG. 10A) and 100B (FIG. 10B) in a substantially circular shape. The second surface 216 of the atomizer cores may have different patterns as illustrated 100A in FIGS. 10A and 10B.

FIGS. 11A and 11B show two atomizer cores 110A (FIG. 11A) with two electrodes 112*a* and 112*b*, and 110B (FIG. 11B) with two electrodes 114*a* and 114*b*. The electrodes 114*a* and 114*b* in atomizer core 110B in FIG. 11B have greater areas than electrodes 112*a* and 112*b* of atomizer core 110A in FIG. 11A.

FIG. 12 shows an atomizer core 120, which has a substantially rectangular body and two arcuate ends. FIG. 13 shows an atomizer core 130 having a substantially rectangular shape.

The atomizer cores described above may also have other shapes or configurations for generating aerosol.

The substrate of the atomization cores 10, 20, 30, and 40, and substrate 50, 60, and 70 discussed above may be manufactured with any one the methods described below.

Through-Glass Via (TGV) Technology

In some examples, the substrate may be a glass substrate, such as glass or single crystal silicon or polycrystal silicon. A method for manufacturing a substrate of an aerosol core, comprises: providing a glass substrate; treating the glass substrate at selected positions with laser to modify a structure of the glass substrate at the selected positions; and etching the glass substrate to form a plurality of the perforations at the selected positions.

The dense glass with high thermal shock properties such as quartz, borosilicate glass and alumina silicate glass, can be drilled using smooth through-glass vias (TGVs) with high aspect ratio (Micromachines 2017, 8, 53; doi:10.3380/mi8020053). TGV may be used to generate a desired perforation array in a glass substrate using the method described above.

TGV includes a laser shining process and a chemical etching process. The laser shining process may use ultra-short laser pulses to modify the structure of the substrate. The perforation array pattern of the glass substrate, such as the distance between adjacent perforations, can be controlled by the laser shining process. For example, the laser shining process can be configured with desired laser spot shape and size. The laser spot shape and size in turn control the size and shape of the perforations to be formed in the glass substrate. In the laser shining process, ultra-short laser pulses may be used to treat one or more surfaces of the glass substrate at selected positions. For example, ultra-short laser pulses may be applied to one or more selected points at the two opposite surfaces of the glass substrate. The ultra-short laser pulse changes the internal structure of the glass substrate at the selected points. The chemical etching process then may be applied to the structurally modified glass substrate at the selected points to generate perforations at the selected points passing through both opposite surfaces of the glass substrate to form microchannels.

The chemical etching process may be wet etching process or dry etching process. Both wet and dry etching processes can be used to prepare the perforations in the glass substrate.

The perforation quality, such as size and/or shape of the perforations, and wall surface of the perforations, can be controlled by the chemical etching process. For example, the dimension of a perforation may be accurately controlled by accurately controlling the etching time. The perforation size can be controlled from a submicron level to several hundred micron level.

As well, with the chemical etching process, the perforation shape can be precisely customized to desired shapes such as true circle, ellipse in horizontal, fixed diameter through perforation, or through perforation tapered from both ends with necking in the middle, or cone shape in vertical. The perforation shape may be selected based on the aerosol source, such as e-juice, THC/CBD, or other medicine and the vaping performances. The shapes of a perforation in the glass substrate can be further adjusted for other vaping requirements, such as for locking aerosol source.

In some examples, the glass substrate may have various thickness, such as less than, equal to or greater than 2 mm. In some cases, the glass substrate thickness can be 1.2 mm, 1 mm, 0.8 mm, 0.6 mm, 0.5 mm, 0.2 mm or less than 0.2 mm. In some cases, for better thermal management, the glass substrate thickness can be about 500 um, or thinner, such as to 50 um.

With the chemical etching process, the perforation size of the glass substrate can be controlled from sub-micro level to 150 um for the vaping application. In some cases, the perforation diameters are controlled below 70 ums. In some examples, the diameter can be 50 um, 30 um, 20 um, 10 um, 5 um or less than 1 um.

As well, TGV can conveniently scale-up the substrate preparation. TGV can be applied to a wafer to simultaneously generate a plurality of substrates or samples. The laser shining process is fast in treating the glass substrate, for example, from 200 perforations per second to over 10000 perforations per second. In comparison, in a laser drilling process to manufacture glass substrate, a single laser can drill about 20 perforations per second. As well, the chemical etching process, such as wet-chemical etching process, can be conducted by batches.

Because the TGV process is a cold treatment process without heating up the glass substrate, the physical property of the glass substrate does not change. As well, TGV does not cause any damage to the mechanical properties of the glass substrate. For example, the TGV does not cause any microcracks in the glass substrate.

TGV on Glass Tubes

As illustrated in FIG. 5, the substrate may have a tubular shape. In some examples, similar to ceramic atomizer cores, the TGV technology can be applied to a tubular glass substrate to form microchannels with desired perforation arrays, for different formation vaping. Unlike ceramic atomizer cores, the glass substrate does not generate particles of crystalized ceramic grainulars, or heavy metals during the ceramic manufacturing process. As well, glass substrate has improved performance in coking, HPHC control, and taste consistency, etc.

As discussed in FIG. 5, the aerosol source and the aerosol are separated by the tubular substrate such as a glass substrate. The aerosol source may be stored inside or outside of the tubular substrate, and the aerosol can be generated at an opposite side of the substrate.

To generate patterned through perforations in the tubular substrate with TGV, the tubular substrate or the laser head can be kept rotating to treat the selected positions in the tubular substrate in order to form patterned perforations. Then wet chemical etching method or dry chemical etching can be applied to the treated positions to generate through vies or perforations at the treated positions.

In some examples, prior to treating a glass substrate, or after etching a glass substrate, a glass annealing process or tempering process may be applied to the glass substrate to enhance the mechanical and thermal performance of the glass substrate, or to form tubular glass substrate by softening roll.

In some examples, after etching a glass substrate, the glass substrate with perforations can also be further machined or treated to different shapes at the softening point of the glass in the glass annealing or tempering process. For example, the glass substrate in the annealing process can be curved to form a tubular glass substrate as described above. In this case, the patterned array of perforations will be substantially kept after the curling process, and the perforation shape may be slightly modified.

TSV (Through-Silicon Via) for Silicon Substrate

TSV may be used to generate perforations in a substrate of single crystal or polycrystal silicon (Silicon substrate). TSV is a vertical connection (via) that passes completely through a silicon wafer or die. In some examples, the substrate of an atomizer core may be single crystal or polycrystal silicon. Both single crystal and polycrystal silicon with microchannels formed by patterned perforations can be also used for general quantum vaping devices or aerosol generating device.

For example, the TSV process may include providing a silicon substrate, photoresist patterning the silicon substrate at selected positions on a surface of the silicon substrate and etching the silicon substrate to form a plurality of the perforations through both the top and bottom surfaces of the silicon substrate.

The etching process can be a wet chemical etching process or a dry chemical etching process for forming the plurality of the perforations. In the wet chemical etching process, different crystal planes have different etching rates. The wet chemical etching process is simple to set up and has high selectivity.

With the TSV process, in some examples, perforations forming the microchannels in the silicon substrate can have diameters from submicrons to 200 um. For example, perforations forming the microchannels in the silicon substrate can have diameters of less than 100 nm.

In the example of the atomizer core 20 in FIG. 3, the substrate mix 22 may be a silicon substrate. A TSV process may be used to generate microchannels in the substrate mix 22 by forming a plurality of perforations at selected positions of the substrate 22. The passive layer 24, and electrodes 26a and 26b may be subsequently formed. In this example, the TSV process has the advantages of TGV, as described in the TGV process.

In the example of the atomizer core 30 in FIG. 4, the silicon substrate 32 may also be formed with the TSV process. The TSV process may generate microchannels in the silicon substrate 32 by forming a plurality of perforations at selected positions of the silicon substrate 32. Then as described in FIG. 4, either diffusion or ion implantation may be used to treat the surface of the silicon substrate 32 to obtain a low resistivity surface layer 34 as the heater for heating the aerosol source. In some examples, the passive layer and/or electrodes may not be necessary since the surface layer 34 can perform both functions. With TSV method, compared with the existing atomizer cores, the atomizer core 30 has a simpler structure by having fewer layers.

In some examples, an anodizing process may be used to manufacture alumina, titanium, zirconia or tantalum oxide substrates. The anodizing process allows the manufacture of substrates for atomizer cores in a large scale.

For example, the anodizing process may be porous anodic alumina (PAA), which is a two-step anodizing process to prepare perforation array alumina substrates. PAA is a self-organized form of aluminum oxide that has a honeycomb-like structure formed by high density arrays of uniform and parallel perforations. Phosphoric acid or other acid treatment in the anodizing process can conveniently adjust the perforation size of PAA substrates for vaping performances.

For example, the perforations may be formed by wet chemical etching in 0.3 M oxalic acid at 40V. The diameter of perforations may be controlled by the time of etching.

In some examples, pre-texturing or imprinting technology may also be used in preparing the substrate. For example, SiC mold with convex nipples may be used to prepare the substrate. The anodizing process may be used to form a regular perforation array in an alumina substrate for an atomizer core. The size of the perforations of the substrate can be in the range from um level to submicron level. Small sizes of the perforations generally can improve oil locking performance and reduce the oil leaking issues for the vaping devices.

The anodizing process can also be employed to prepare regulated titanium, zirconium, or tantalum substrates, porous anodic $TiO_2$ tubes (PATT), zirconia substrates, tantalum oxide substrates and other biocompatible substrates for atomizer cores.

With porous anodizing oxide (PAO), the perforation size can be controlled to submicron level, and that the distance between perforation walls is uniform. This in turn improves both in-situ vaping and oil-locking performance of the substrates. For example, the substrate may be aluminum, and the perforation size can be less than 100 nm.

Electrochemical Corrosion Perforation Technology (ECPT)

In some examples, the substrate of an atomizer core may be manufactured by using microelectrode array to electronically drill perforations on the substrate. The substrates may be silicon wafers, glasses, and dense ceramics.

With ECPT, the perforation size and speed of generating perforations can be conveniently controlled. For example, the etching speed can be controlled by the electrical current.

For example, silicon wafers or glasses may be placed in a 20% sodium bicarbonate solution in an electrolytic cell. The substrate may be placed on the negative electrode of the electrolytic cell. The perforation probe array, such as a tungsten perforation probe array, is used as the anode of the electrolytic cell. The anode may also be an electrode pin array. The perforation probe is connected in series with a current limiting resistor. A pulsating DC voltage, for example in a range of 40-100V, is applied between the perforation probe array and the negative electrode to generate perforations at selected points of the substrate.

The electrochemical process can quickly and effectively corrode the substrate and then form a perforation array without damage to the substrates.

The microelectrode has the advantages of TGV and TSV as described above. As well, by using microelectrode, the perforation size and the drilling speed can be controlled very well with the copy to the microelectrode array.

Compared with existing substrate manufacturing processes, the drilling process of the substrate of an atomizer core using the TGV, TSV, anodizing process, or CEPT process has better perforation quality control and avoids damage to the substrate in the drilling process. The mechanical performance and thermal performance of the substrate can be substantially the same as the bulk material of the substrate before the drilling process. As well, the perforation size can be customized to the requirements of the vaping performances, for example, from 200 um diameter to a submicron level. The balance between the aerosol source springing out and leaking can be conveniently adjusted by the selection of proper perforation size. Each of the TGV, TSV, anodizing process, and CEPT process allows high volume and high yield manufacturing with low cost by manufacturing in a large scale.

Certain adaptations and modifications of the described embodiments can be made. Therefore, the above discussed embodiments are considered to be illustrative and not restrictive.

What is claimed is:

1. An atomizer core for an aerosol generating device, the atomizer core comprising:

a core body having a first surface and a second surface, said core body including a substrate and a separate heater disposed between said first surface and said second surface, said heater being deposited as a layer or film over said substrate proximate to said second surface; and a plurality of channels extending between said first surface and said second surface for transferring an aerosol precursor from said first surface through said substrate and said heater to said second surface, said heater being adapted to heat the aerosol precursor to form an aerosol at said second surface.

2. The atomizer core of claim 1, wherein said substrate comprises glass.

3. The atomizer core of claim 1, wherein said substrate comprises crystal.

4. The atomizer core of claim 1, wherein said substrate comprises silicon.

5. The atomizer core of claim 1, wherein said substrate comprises silicon carbide.

6. The atomizer core of claim 1, wherein said substrate comprises is not electrically conductive materials.

7. The atomizer core of claim 1, wherein said core body has a uniform thickness.

8. The atomizer core of claim 1, wherein said plurality of channels have a uniform size.

9. The atomizer core of claim 1, wherein said plurality of channels have a uniform diameter.

10. The atomizer core of claim 1, wherein said plurality of channels have a uniform cross-sectional shape.

11. The atomizer core of claim 1, wherein said plurality of channels have a uniform distribution.

12. The atomizer core of claim 1, wherein said plurality of channels each have a diameter of 250 microns or less.

13. The atomizer core of claim 1, wherein said plurality of channels each have a diameter of 50 microns or less.

14. The atomizer core of claim 1, further comprising an insulator disposed between said substrate and said heater, said plurality of channels extending through said substrate, said insulator and said heater for transferring an aerosol precursor from said first surface to said second surface, wherein said insulator is adapted to insulate said substrate at least partially from heat generated by said heater.

15. The atomizer core of claim 14, wherein said insulator is made from a low thermal conductive material.

16. The atomizer core of claim 14, wherein said insulator comprises $Al2O3$, $SiO2$, $ZrO2$, $HfO2$, ZnO, or $TiO2$.

17. The atomizer core of claim 1, further comprising a passive layer disposed on said heater to prevent oxidation.

18. The atomizer core of claim 17, wherein said passive layer comprises Au, Au—Ag alloy, Pt or Pd—Ag alloy.

19. The atomizer core of claim 1, wherein said second surface opposes said first surface.

20. The atomizer core of claim 1, wherein said first surface and said second surface are each planar.

21. The atomizer core of claim 1, wherein said first surface and said second surface are each tubular.

22. The atomizer core of claim 1, further comprising a plurality of electrode contacts for supplying power from a power source to said heater.

23. The atomizer core of claim 1, wherein said heater comprises bio-compatible metals or bio-compatible metals based alloys, or Ni—Cr based alloys.

24. The atomizer core of claim 23, wherein the bio-compatible metals comprise Al, Ti, Ta, Zr, Pt, Au, Ag, Pd, Re, Yb, Y, Ce, La, Hf, Si, alloys based thereon, Ni—Cr alloys, or medical stainless steel.

25. An aerosol generating device comprising an atomizer core as claimed in claim 1.

* * * * *